United States Patent [19]

Blakeney et al.

[11] Patent Number: 5,547,814

[45] Date of Patent: Aug. 20, 1996

[54] O-QUINONEDIAZIDE SULFONIC ACID ESTERS OF PHENOLIC COMPOUNDS AND THEIR USE IN FORMING POSITIVE IMAGES

[75] Inventors: Andrew J. Blakeney, Seekonk, Mass.; Arturo N. Medina, Pawtucket; Medhat A. Toukhy, Barrington, both of R.I.; Lawrence Ferreira, Fall River; Sobhy Tadros, Seekonk, both of Mass.

[73] Assignee: OCG Microelectronic Materials, Inc., Norwalk, Conn.

[21] Appl. No.: 451,599

[22] Filed: May 26, 1995

Related U.S. Application Data

[62] Division of Ser. No. 384,501, Feb. 1, 1995.

[51] Int. Cl.$^6$ .................... G03F 7/30; G03F 7/023
[52] U.S. Cl. ............. 430/326; 430/165; 430/191; 430/192; 430/193; 430/330
[58] Field of Search .................... 430/325, 326, 430/191, 192, 193, 165, 330

[56] References Cited

U.S. PATENT DOCUMENTS

| | | | |
|---|---|---|---|
| 5,173,389 | 12/1992 | Uenishi et al. | 430/192 |
| 5,294,521 | 3/1994 | Jacovich et al. | 430/192 |
| 5,407,779 | 4/1995 | Uetani et al. | 430/192 |

FOREIGN PATENT DOCUMENTS

| | | |
|---|---|---|
| 573056 | 4/1993 | European Pat. Off. . |
| 570884 | 5/1993 | European Pat. Off. . |

Primary Examiner—John S. Y. Chu
Attorney, Agent, or Firm—William A. Simons

[57] ABSTRACT

A photosensitive compound comprising at least one o-quinonediazide sulfonic acid ester of a phenolic compound, said esters selected from the group consisting of formulae (IB) and (IIB):

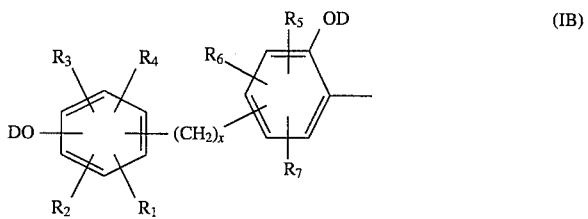

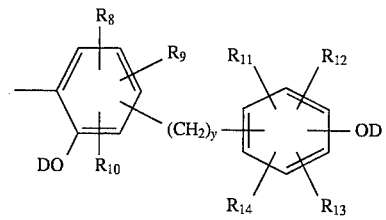

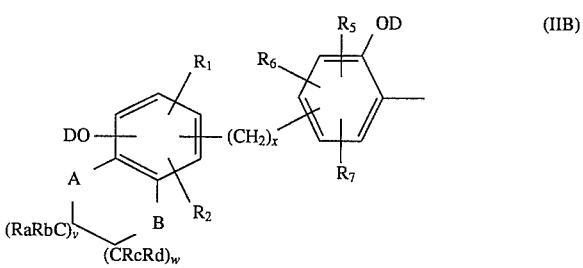

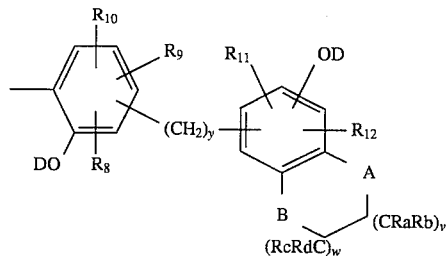

wherein the photosensitive compound is used in a radiation sensitive composition and a process for forming a positive patterned image.

16 Claims, No Drawings

O-QUINONEDIAZIDE SULFONIC ACID ESTERS OF PHENOLIC COMPOUNDS AND THEIR USE IN FORMING POSITIVE IMAGES

This application is a division of U.S. application Ser. No. 08/384,501 filed Feb. 1, 1995 which is incorporated herein by reference in its entirety.

BACKGROUND OF THE INVENTION

1. Field of the Invention

The present invention relates to certain four aromatic ring structures having a 2,2'biphenol nuclei. The present invention also relates to photosensitive o-quinonediazide sulfonic acid esters of these ring structures. Still further, the present invention also relates to radiation sensitive mixtures (e.g., those particularly useful as positive-working photo-resists) containing the combination of these photoactive compounds with alkali-soluble binder resins dissolved in a solvent. And furthermore, the present invention also relates to substrates coated with these radiation sensitive mixtures as well as the process of coating, imaging and developing these radiation sensitive mixtures on these substrates.

2. Description of the Related Art

Photoresist compositions are used in microlithographic processes for making miniaturized electronic components such as in the fabrication of integrated circuits and printed wiring board circuitry. In these processes, a thin coating or film of a photoresist composition is generally first applied to a substrate material, such as silicon wafers used for making integrated circuits or aluminum or copper plates of printed wiring boards. The coated substrate is then baked to evaporate any solvent in the photoresist composition and to fix the coating onto the substrate. The baked coated surface of the substrate is next subjected to an image-wise exposure of radiation. This radiation exposure causes a chemical transformation in the exposed areas of the coated surface. Visible light, ultraviolet (UV) light, electron beam, ion beam and X-ray radiant energy are radiation types commonly used today in microlithographic processes.

After this image-wise exposure, the coated substrate is treated with a developer solution to dissolve and remove either the radiation-exposed or the unexposed areas of the coated surface of the substrate. In some processes, it is desirable to bake the imaged resist coating before this developing step. This intermediate step is sometimes called post-exposure bake or PEB.

There are two types of photoresist compositions—negative-working and positive-working. When negative-working photoresist compositions are exposed image-wise to radiation, the areas of the resist composition exposed to the radiation become less soluble to a developer solution (e.g., a cross-linking reaction occurs) while the unexposed areas of the photoresist coating remain relatively soluble to a developing solution. Thus, treatment of an exposed negative-working resist with a developer solution causes removal of the nonexposed areas of the resist coating and the creation of a negative image in the photoresist coating, and thereby uncovering a desired portion of the underlying substrate surface on which the photoresist composition was deposited. On the other hand, when positive-working photoresist compositions are exposed image-wise to radiation, those areas of the resist composition exposed to the radiation become more soluble to the developer solution (e.g., the Wolff rearrangement reaction of the photoactive compound occurs) while those areas not exposed remain relatively insoluble to the developer solution. Thus, treatment of an exposed positive-working resist with the developer solution causes removal of the exposed areas of the resist coating and the creation of a positive image in the photoresist coating. Again, a desired portion of the underlying substrate surface is uncovered.

Positive-working photoresist compositions are currently favored over negative-working resists because the former generally have better resolution capabilities and pattern transfer characteristics.

After this development operation, the now partially unprotected substrate may be treated with a substrate etchant solution or plasma gases and the like. This etchant solution or plasma gases etch the portion of the substrate where the photoresist coating was removed during development. The areas of the substrate are protected where the photoresist coating still remains and, thus, an etched pattern is created in the substrate material which corresponds to the photomask used for the image-wise exposure of the radiation. Later, the remaining areas of the photoresist coating may be removed during a stripping operation, leaving a clean etched substrate surface. In some instances, it is desirable to heat treat the remaining resist layer after the development step and before the etching step to increase its adhesion to the underlying substrate and its resistance to etching solutions. End users of photoresists are demanding photoresist formulations which possess better lithographic properties for the fabrication of smaller microelectronic circuits. The lithographic properties which are critical to these end-users include the following: (1) resolution capabilities in both the micron and submicron ranges without incomplete development in the exposed areas (i.e., scumming); (2) higher thermal image deformation temperatures (e.g. above 120° C.); (3) relatively fast photospeeds; (4) good adhesion to substrate; (5) good developer dissolution rates; (6) wide process latitude; (7) near to absolute vertical profiles (or good contrast) between exposed and unexposed photoresist areas after development; (8) good resistance to etching solutions and plasma etching techniques; (9) reduced tendency to form insoluble particulates; (10) mask linearity; and (11) low metal contamination.

Generally, in the past efforts to improve one of these lithographic properties have caused significant decreases in one or more of the other lithographic properties of the photoresist. Accordingly, there is a need for improved photoresist formulations which possess all of these desired properties. The present invention is believed to be an answer to that need.

For example, while photosensitive compounds are essential to obtain the positive images of positive-working photoresists, such photosensitive compounds are sometimes not soluble for extended time periods in photoresist formulations. They may also contribute to the degradation of photoresist formulations by chemical reaction. Still further, certain photoactive compounds may contribute to scumming, causing the degradation of the thermal profile, and contributing to the lowering of the thermal deformation temperature of the resist patterns. Selection of a suitable photoactive compound without those weaknesses is a difficult and not a totally predictable task.

SUMMARY OF THE INVENTION

Accordingly, one aspect of the present invention is directed to phenolic compound selected from the group consisting of formulae (IA) and (IIA):

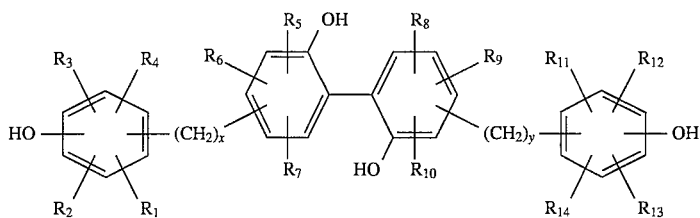

(IA)

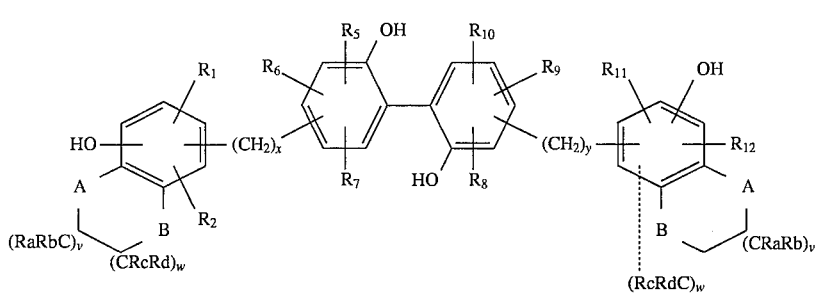

(IIA)

wherein $R_1$, $R_2$, $R_{11}$, and $R_{12}$ are each independently selected from the group consisting of hydrogen, hydroxyl, halogen, lower alkyl group having 1 to 4 carbon groups, lower alkyl ether groups having 1 to 4 carbon atoms and lower alkyl thioether groups having 1 to 4 carbon atoms;

wherein $R_3$, $R_4$, $R_5$, $R_6$, $R_7$, $R_8$, $R_9$, $R_{10}$, $R_{13}$, and $R_{14}$ are each independently selected from the group consisting of hydrogen, halogen, lower alkyl groups having 1 to 4 carbon atoms, lower alkyl ether group having 1 to 4 carbon atoms and lower alkyl thioether groups having 1 to 4 carbon groups;

wherein x and y are each independently selected from an integer from the group 0, 1, 2, 3, and 4;

wherein Ra, Rb, Rc, and Rd are each independently selected from hydrogen and a lower alkyl group having 1 to 4 carbon atoms;

wherein v and w are each independently selected from an integer from the group 0 and 1 and each sum of v and w on a fused ring equals 1 or 2; and wherein A and B are each independently selected from the group consisting of oxygen, sulfur, and a methylene radical.

Another aspect of the present invention is directed to photosensitive compound comprising at least one o-quinonediazide sulfonic acid ester of a phenolic compound, said esters selected from the group consisting of formulae (IB) and (IIB):

wherein $R_1$, $R_2$, $R_{11}$, and $R_{12}$ are each independently selected from the group consisting of hydrogen, OD, halogen, lower alkyl group having 1 to 4 carbon atoms, lower alkyl ether groups having 1 to 4 carbon atoms, and lower alkyl thioether groups having 1 to 4 carbon atoms;

wherein $R_3$, $R_4$, $R_5$, $R_6$, $R_7$, $R_8$, $R_9$, R10, $R_{13}$, and $R_{14}$ are each independently selected from the group consisting of hydrogen, halogen, lower alkyl groups having 1 to 4 carbon atoms lower alkyl ether groups having 1 to 4 carbon atoms; and lower alkyl thioether groups having 1 to 4 carbon groups;

wherein x and y are each independently selected from an integer from the group 0, 1, 2, 3, and 4;

wherein Ra, Rb, Rc, and Rd are each independently selected from hydrogen and a lower alkyl group having 1 to 4 carbon atoms;

wherein v and w are each independently selected from an integer from the group 0 and 1 and each sum of v and w on a fused ring is 1 or 2; and wherein A and B are each independently selected from the group consisting of oxygen, sulfur, and a methylene radical; and wherein each OD group is a hydroxyl or an o-quinonediazide sulfonic acid ester group wherein each D is selected from the group consisting of naphthoquinonediazide sulfonyl group or benzoquinonediazide sulfonyl group, provided that

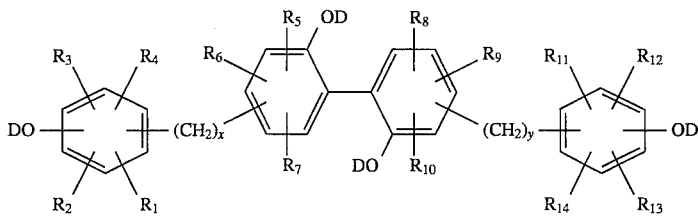

(IB)

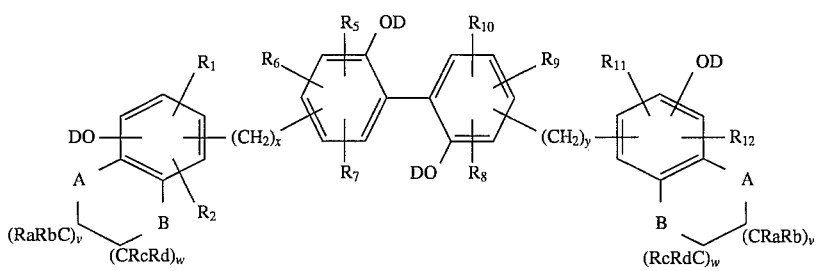

(IIB)

at least one —OD is an o-quinonediazide sulfonic acid ester group.

Moreover, the present invention is directed to a radiation sensitive mixture useful as a positive photoresist comprising an admixture of at least one photosensitive compound of formula (IB) or (IIB) above and an alkali-soluble binder resin; the amount of said photoactive o-naphthoquinone diazide compound or compounds being about 5% to about 40% by weight based on the total solids content of said radiation sensitive mixture.

Still further, the present invention also encompasses the process of coating substrates with these radiation sensitive mixtures and then exposing and developing these coated substrates.

Also further, the present invention encompasses said coated substrates (both before and after imaging) as novel articles of manufacture.

Another aspect of the present invention is a positive photoresist composition comprising an admixture of an alkali soluble resin and a photoactive compound comprising quinonediazide sulfonic acid ester of a phenol compound; wherein: (a) said phenol compound has no less than four phenolic hydroxyl groups, and (b) wherein a HPLC peak area corresponding to the quinonediazide sulfonic acid triesters is greater than or equal to 50% of all HPLC peak areas corresponding to the photoactive compounds in said HPLC spectrum; said HPLC spectrum measured with a primary detector using UV light having the wavelength of 254 nm.

And a further aspect of the present invention is a positive photoresist composition comprising an admixture of an alkali soluble resin and a photoactive compound comprising quinonediazide sulfonic acid esters of two or more phenolic compounds, wherein:

(a) the phenolic compounds each having either three or four phenolic hydroxyl groups;

(b) the HPLC peak area corresponding to quinonediazide sulfonic acid triesters of the phenolic compounds is greater than or equal to 45% of the total HPLC peak area of all quinonediazide sulfonic acid esters;

(c) the HPLC peak area corresponding to quinonediazide sulfonic acid diesters is less than or equal to 40% of the total HPLC peak area of all quinonediazide sulfonic acid esters; and (d) the HPLC peak area corresponding to the quinonediazide sulfonic acid triester of the phenolic compounds having 3 hydroxyl groups is less than or equal to 20% of the total HPLC peak area of all quinonediazide sulfonic acid esters; said HPLC spectrum measured with a primary detector using UV light having the wavelength of 254 nm.

DESCRIPTION OF PREFERRED EMBODIMENTS

The aromatic ring structures of formula (IA) and (IIA) having a 2,2'biphenol nuclei are preferably made by a three-step reaction sequence. The first step is a coupling reaction of a mono-ring phenolic precursor into a 2,2'biphenol compound by a ring-ring bond. This is preferably carried out in the presence of an enzyme catalyst such as soybean peroxidase at a slightly elevated temperature. One preferred precursor is vanillin. This coupling reaction converts the vanillin to dehydrodivanillin.

The second step in the reaction sequence is an aldehyde reduction step. Any aldehyde substituents on the phenolic rings are converted to the corresponding alcohol groups. In the case of dehydrodivanillin, it is converted to dehydrodivanillin alcohol. Any conventional aldehyde reduction reaction conditions may be used for this step. For example, this reaction may be carried out with sodium borohydride in a tetrahydrofuron/methanol reaction mixture or with hydrogen in the presence of a catalyst such as raney nickel.

The third reaction step in this particular synthesis of making the 4-ring compounds are made by reacting the reduced reaction product of the second step with one or more phenolic moieties preferably such as phenol, o-cresol, m-cresol, p-cresol, 2,3-dimethylphenol, 2,5-dimethylphenol, 2,6-dimethylphenol, 3,4-dimethylphenol, 3,5-dimethylphenol, and the like. This reaction step may be carried out using any suitable condensation/addition reaction conditions. In this reaction, the alcohol substituents on the reaction product of step two are converted to the corresponding alkylene radical (e.g., methylene) that connects the phenolic ring together (i.e., $(CH_2)_x$ and $(CH_2)_y$ in formula IA and IIA). Of course, where x and y= o, the second step of the above reaction sequence may be omitted and any suitable ring-ring bond forming reaction may be employed instead of the condensation step. Another precursor besides divanillin is ethyldivanillin.

The aromatic ring structure of formula (IA) and (IIA) may be converted into photosensitive compounds by reacting those compounds with an o-quinonediazide sulfonyl halide (e.g., napthoquinonediazide sulfonyl halogenide or a benzoquinonediazide sulfonyl halogenide) using conventional reaction conditions.

The most preferred o-naphthoquinone diazide sulfonyl ester moieties are derived from 3-diazo-3,4-dihydro-4-oxonaphthalene-sulfonic acid chloride (also known as 1,2-naphthoquinone-(2)-diazo- 4-sulfonic acid chloride or Diazo M) or 6-diazo-5,6-dihydro-5-oxonaphthalene-1-sulfonic acid chloride (also known as 1,2-naphthaquinone-(2)-diazo-5-sulfonic acid chloride or Diazo L). These 4- and 5-ester groups or moieties respectively have the following chemical formulae (A) and (B):

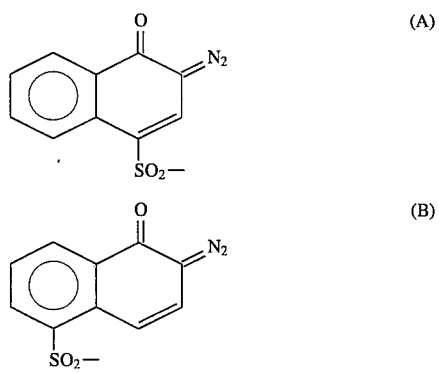

Other suitable o-quinonediazide sulfonyl moieties are represented by the following formula (C) and (D):

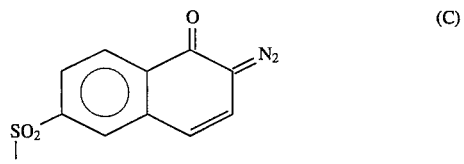

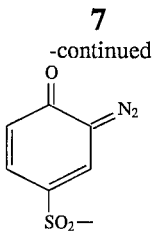
(D)

It is understood that the present invention covers the use of o-quinonediazide sulfonyl moieties singly or in mixtures in the condensation reaction with these compounds of formulae (IA) or (IIA). Also, the present invention encompasses separate reactions of these compounds with different o-naphthoquinone diazide sulfonyl moieties followed by blending those reaction products together.

This condensation reaction may be carried under any conventional ester condensation conditions. Preferably, the photosensitive ester compounds of formulae (IB) and (IIB), above, are prepared by first dissolving the sulfonic acid halide precursor, preferably, the sulfonic acid chloride, in a suitable solvent. Suitable solvents include acetone, dioxane, gamma-butyrolactone, methylene chloride, tetrahydrofurfural alcohol and the like. The compound of formulae (IA) or (IIA) is then added to this solution. It is advantageous to carry out this reaction in the presence of an acid-scavenging base, such as alkali metal carbonates or bicarbonates, alkaline earth metal carbonates or bicarbonates, tertiary aliphatic amines or pyridine or pyridine derivatives.

The esterification products of this reaction may be recovered from the reaction mixture by any conventional means, preferably by precipitation into acidified water, followed by filtration and drying.

The preferred photosensitive compounds (sometimes also referred to as "photoactive compounds) when said compound is of formula (IB) are those where $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently selected from hydrogen, a lower alkyl group having 1 to 4 carbon atoms or lower alkoxy group having 1 to 4 carbon atoms and $x=y=1$, 2, or 3. It should be noted that a lower alkoxy group is one species of a lower alkyl ether group.

The preferred photosensitive compounds of formula (IIB) are those where $R_1$, $R_2$, $R_5$, $R_6$, $R_7$, $R_8$, $R_9$, $R10$, $R_{11}$, and $R_{12}$ are independently selected from hydrogen, a lower alkyl group having 1 to 4 carbon atoms, a lower alkoxy group having 1 to 4 carbon atoms; and Ra, Rb, Rc, and Rd are each independently selected from hydrogen or a methyl group; and A and B are each independently selected from oxygen or a methylene radical.

More preferably, each D in formulae (IB) and (IIB), above, and the formulae below are preferably naphthoquinone-(1,2)-diazide-5-sulfonyl; naphthoquinone-(1,2)-diazide-4-sulfonyl or hydrogen, with the proviso that at least two of the D groups are not hydrogen.

Specific examples of photosensitive compounds of formulae (IB) and (IIB) are shown by the following formulae (III) to (XII):

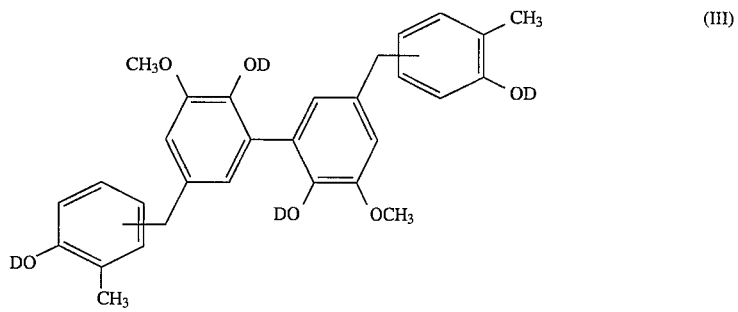
(III)

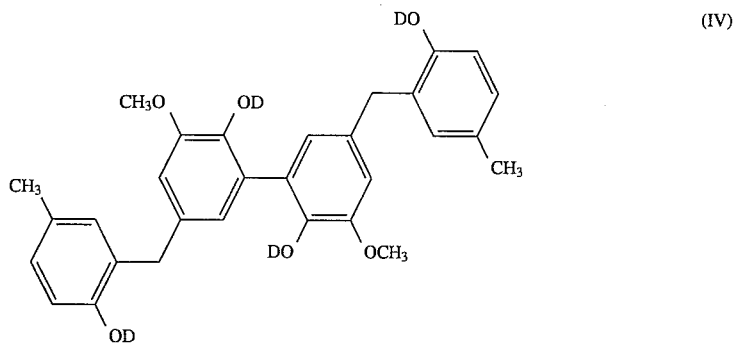
(IV)

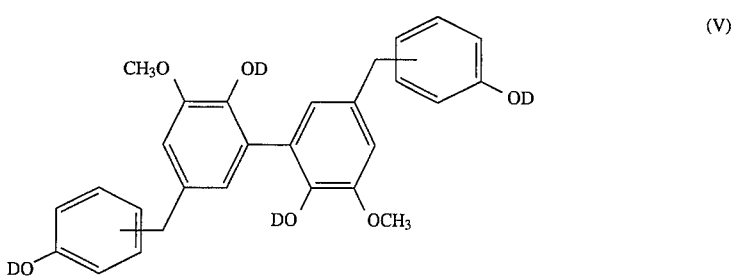
(V)

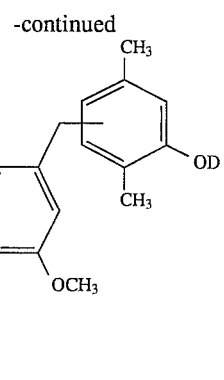
(VI)
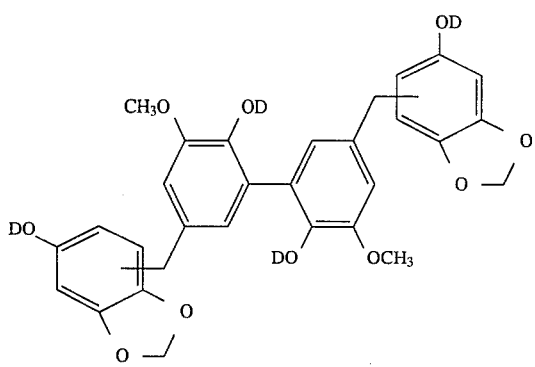
(VII)
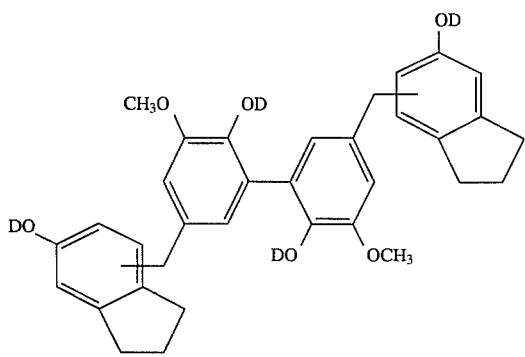
(VIII)
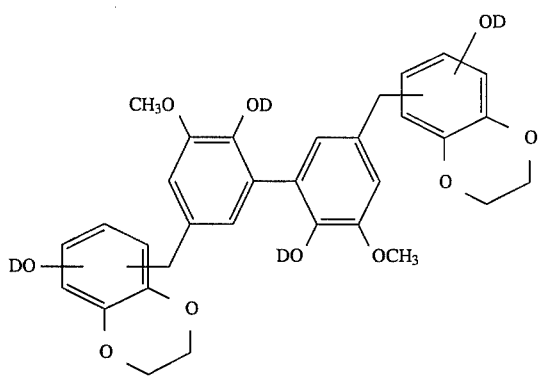
(IX)

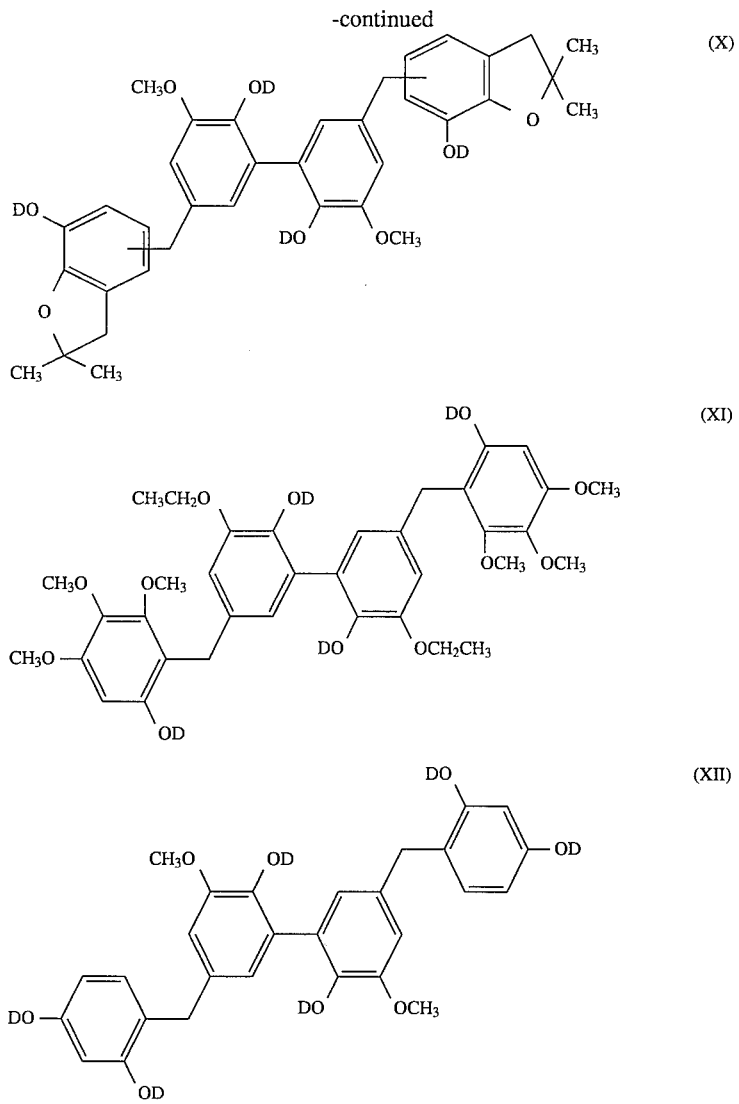

At least one of the ester compounds of the present invention may be mixed with an alkali-soluble resin or resins to make radiation sensitive mixtures which are useful as positive-working photoresist compositions. The term "alkali-soluble resin" is used herein to mean a resin which will dissolve completely in an aqueous alkaline developing solution conventionally used with positive-working photoresist compositions. Suitable alkali-soluble resins include phenol-formaldehyde novolak resins, cresol-formaldehyde novolak resins, and polyvinyl phenol resins, preferably having a molecular weight of about 500 to about 40,000, and more preferably from about 800 to 20,000. These novolak resins are preferably prepared by the condensation reaction of phenol or cresols with formaldehyde and are characterized by being light-stable, water-insoluble, alkali-soluble and film-forming. One preferred class of novolak resins is formed by the condensation reaction between a mixture of meta- and para-cresols with formaldehyde having a molecular weight of about 1,000 to about 10,000. The preparation of examples of such suitable resins is disclosed in U.S. Pat. Nos. 4,377,631; 4,529,682; and 4,587,196, all of which issued to Medhat Toukhy and are incorporated herein by reference in their entireties. Other preferred novolaks are shown in U.S. Pat. Nos. 5,237,037; 5,322,757; and 5,324,620 (issued to Charles Ebersole) and are also incorporated herein by reference in their entireties.

Other photoactive compounds may also be added to the radiation sensitive mixtures of the present invention. These other photosensitive compounds may include o-quinonediazide esters derived from polyhydric phenols, alkyl-polyhydroxyphenones, aryl-polyhydroxyphenones, and the like which can contain up to six or more sites for esterification. The most preferred o-quinonediazide esters are derived from 3-diazo-3,4-dihydro-4-oxonaphthalene-sulfonic acid chloride or 6-diazo-5,6-dihydro- 5-oxonaphthalene-1-sulfonic acid chloride. When other photosensitive compounds are used in radiation sensitive mixtures besides the photosensitive compounds of the present invention, the amount of photosensitive compounds of the present invention should be at least about 5% by weight, preferably 10–100% by weight of the total photosensitive compounds present.

Examples of preferred other photosensitive compounds include compounds having the following chemical formulae (E), (F), and (G):

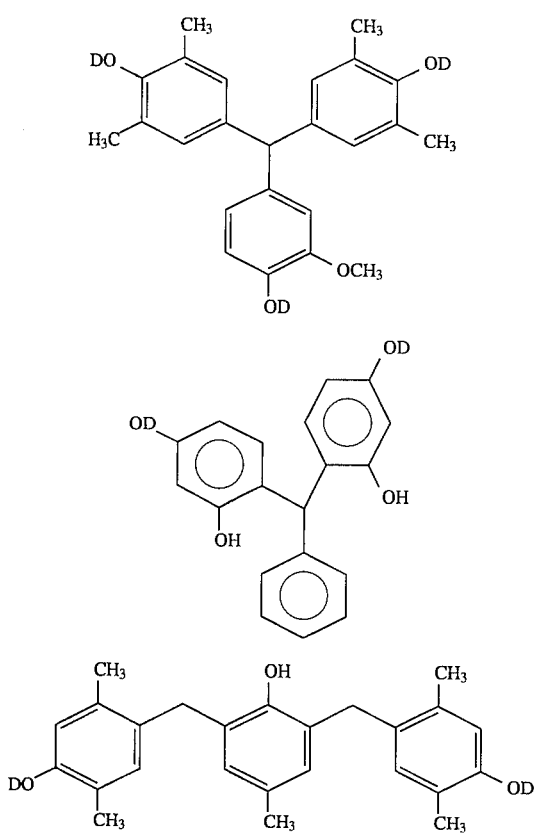

In each formula, each D is

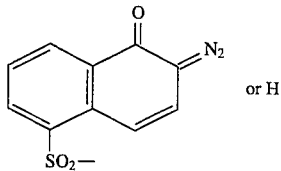

or H with the proviso that not all D groups are hydrogen.

If the photosensitive compound of formula (IB) or (IIB) is employed in a radiation sensitive composition that quinonediazide sulfonic acid ester is preferably of a phenol compound having four phenolic hydroxy groups and the HPLC peak area corresponding to the quinonediazide triesters is greater than or equal to 60% of all HPLC peak areas corresponding to photosensitive compounds in said HPLC spectrum.

Where the photosensitive compound in a positive photoresist comprises quinonediazide sulfonic acid esters of two phenolic compounds, preferably one of those phenolic compounds has three hydroxyl groups and the other has four hydroxyl groups; wherein the HPLC peak area corresponding to quinonediazide sulfonic acid triesters of the phenolic compounds is greater than or equal to 50% of the total HPLC peak area of all quinonediazide sulfonic acid esters; and wherein said HPLC peak area corresponding to quinonediazide sulfonic acid diesters is less than or equal to 35% of the total HPLC peak area of all quinonediazide sulfonic acid esters.

The proportion of the photoactive compound in the radiation sensitive mixture may preferably range from about 5 to about 40%, more preferably from about 8 to about 30% by weight of the nonvolatile (e.g., nonsolvent) content of the radiation sensitive mixture.

These radiation sensitive mixtures may also contain conventional photoresist composition ingredients such as solvents, actinic and contrast dyes, anti-striation agents, plasticizers, speed enhancers, and the like. These additional ingredients may be added to the binder resin and photoactive compound before the solution is coated onto the substrate. The proportion of the sum of binder resin and speed enhancers of this present invention in the radiation sensitive mixture may preferably range from about 50 to about 95%, more preferably, from about 70 to 92% of the nonvolatile (e.g., excluding solvents) solids content of the radiation sensitive mixture.

The preferred relative amount of speed enhancer in a positive resist is from 0% to about 40%, more preferably from about 15% to about 35% by weight, based on the total weight of all binder resins and speed enhancers in the resist.

The resins and sensitizers may be dissolved in a solvent or solvents to facilitate their application to the substrate. Examples of suitable solvents include methoxyacetoxy propane, ethyl cellosolve acetate, n-butyl acetate, ethyl lactate, ethyl 3-ethoxy propionate, methyl-3-methoxypropionate propylene glycol alkyl ether acetates, or mixtures thereof and the like. Cosolvents such as xylene or n-butylacetate may also be used. The preferred amount of solvent may be from about 50% to about 500%, or higher, by weight, more preferably, from about 100% to about 400% by weight, based on combined resin and sensitizer weight. Actinic dyes help provide increased resolution on highly reflective surfaces by inhibiting back scattering of light off the substrate. This back scattering causes the undesirable effect of optical notching, especially on a highly reflective substrate topography. Examples of actinic dyes include those that absorb light energy at approximately 400–460 nm [e.g. Fat Brown B (C.I. No. 12010); Fat Brown RR (C.I. No. 11285); 2-hydroxy-1,4-naphthoquinone (C.I. No. 75480) and Quinoline Yellow A (C.I. No. 47000)] and those that absorb light energy at approximately 300–340 nm [e.g., 2,5-diphenyloxazole (PPO-Chem. Abs. Reg. No. 92-71-7) and 2-(4-biphenyl)-6-phenylbenzoxazole (PBBO-Chem. Abs. Reg. No. 17064-47-0)]. Another preferred dye is BLANKOPHOR FBW active dye available from Mobay. The use of this dye in positive resists is covered by U.S. Pat. No. 5,275,909, which issued to T. V. Jayaraman and is incorporated herein by reference in its entirety. The amount of actinic dyes may be up to ten percent weight levels, based on the combined weight of resin and sensitizer.

Contrast dyes enhance the visibility of the developed images and facilitate pattern alignment during manufacturing. Examples of contrast dye additives that may be used together with the radiation sensitive mixtures of the present invention include Solvent Red 24 (C.I. No. 26105), Basic Fuchsin (C.I. 42514), Oil Blue N (C.I. No. 61555) and Calco Red A (C.I. No. 26125) up to 10% weight levels, based on the combined weight of resin and sensitizer.

Anti-striation agents or leveling agents level out the resist coating or film to a uniform thickness. In other words, the leveling agent is used to eliminate the formation of striations on the surface of the resist coating once the coating is spun onto the substrate surface. Anti-striation agents may be used up to 5% weight levels, based on the weight of solids in the resist formulation. One suitable class of anti-striation agents is nonionic silicon-modified polymers. A preferred one is TROYKYD 366 made by Troy Chemical Co., Newark, N.J. Another suitable class of anti-striation agents is fluoroaliphatic polymeric ester surfactants. A preferred one is FC-430 FLUORAD made by 3M of St. Paul, Minn. Nonionic surfactants may also be used for this purpose, including, for example nonylphenoxy poly(ethyleneoxy) ethanol; octylphenoxy (ethyleneoxy) ethanol; and dinonyl phenoxy poly(ethyleneoxy) ethanol; polyoxyethylene lauryl ether; polyoxyethylene oleyl ether; polyoxyethylene octylphenyl ether; polyoxyethylene nonylphenyl ether; poly-oxyethylene glycol dilaurate; and polyoxyethylene glycol distearate. Also may be useful are organosiloxane polymers and acrylic acid-containing or methacrylate acid-containing polymers.

Plasticizers improve the coating and adhesion properties of the photoresist composition and better allow for the application of a thin coating or film of photoresist which is smooth and of uniform thickness onto the substrate. Plasticizers which may be used include, for example, phosphoric acid tri-(β-chloroethyl)-ester; stearic acid; dicamphor; polypropylene; acetal resins; phenoxy resins; and alkyl resins up to ten percent weight levels, based on the combined weight of resin and sensitizer.

Speed enhancers tend to increase the solubility of the photoresist coating in both the exposed and unexposed areas, and thus, they are used in applications where speed of development is the overriding consideration even though some degree of contrast may be sacrificed, i.e., in positive resists while the exposed areas of the photoresist coating will be dissolved more quickly by the developer, the speed enhancers will also cause a larger loss of photoresist coating from the unexposed areas. Speed enhancers that may be used include, for example, picric acid, nicotinic acid or nitrocinnamic acid, as well as poly(monohydric)phenolic compounds at weight levels of up to 40%, preferably from 10% to 35%, based on the combined weight of resin and sensitizer. The optimum amount of speed enhancer will depend upon the dissolution rates of binder resin and speed enhancers employed as well as the developer used.

Particularly preferred speed enhancers have chemical formulae (H), (J), and (K) shown as follows:

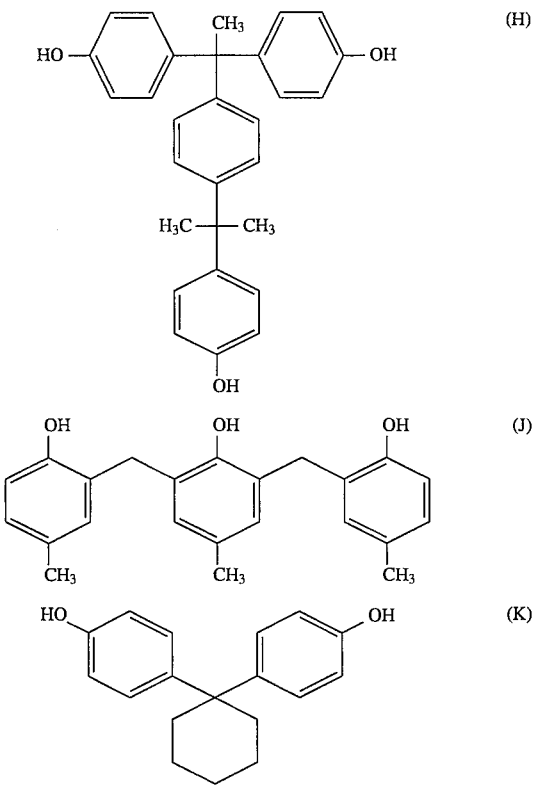

The prepared radiation sensitive resist mixture, can be applied to a substrate by any conventional method used in the photoresist art, including dipping, spraying, whirling and spin coating. When spin coating, for example, the resist mixture can be adjusted as to the percentage of solids content in order to provide a coating of the desired thickness given the type of spinning equipment and spin speed utilized and the amount of time allowed for the spinning process. Suitable substrates include silicon, aluminum or polymeric resins, silicon dioxide, doped silicon dioxide, silicon resins, gallium arsenide, silicon nitride, tantalum, copper, polysilicon, ceramics and aluminum/copper mixtures. The coating surfaces of these substrates may or may not be primed with a conventional adhesion promoter (e.g., hexamethyldisilazane) before the photoresist coating is applied.

The photoresist coatings produced by the above described procedure are particularly suitable for application to silicon wafers coated with a silicon dioxide or silicon nitride layer such as are utilized in the production of microprocessors and other miniaturized integrated circuit components. An aluminum or aluminum-coated substrates may be used as well. The substrate may also comprise various polymeric resins especially transparent polymers such as polyesters and polyolefins.

After the resist solution is coated onto the substrate, the coated substrate is baked at approximately 70° C. to 125° C. until substantially all the solvent has evaporated and only a uniform radiation sensitive coating remains on the substrate. The coated substrate can then be exposed to radiation, especially ultraviolet radiation, in any desired exposure pattern, produced by use of suitable masks, negatives, stencils, templates, and the like. Conventional imaging process or apparatus currently used in processing photoresist-coated substrates may be employed with the present invention. While ultraviolet (UV) light is the preferred source of radiation, other sources of radiation such as visible light, electron or ion beam and X-ray radiant energy may be used instead.

The exposed resist-coated substrates are preferably subjected to a post exposure bake at a temperature from about 100° C. to about 130° C. from about 30–300 seconds to enhance image quality and resolution. The exposed resist-coated substrates are next developed in an aqueous alkaline solution. This solution is preferably agitated, for example, by nitrogen gas. Examples of aqueous alkaline developers include aqueous solutions of tetramethylammonium hydroxide, sodium hydroxide, potassium hydroxide, ethanolamine, choline, sodium phosphates, sodium carbonate, sodium metasilicate, and the like. The preferred developers for this invention are aqueous solutions of either alkali metal hydroxides, phosphates or silicates, or mixtures thereof, or tetramethylammonium hydroxide.

Preferred development techniques include spray development or puddle development, or combinations thereof, may also be used.

The substrates are allowed to remain in the developer until all of the resist coating has dissolved from the exposed areas. Normally, development times from about 10 seconds to about 3 minutes are employed.

After selective dissolution of the coated wafers in the developing solution, they are preferably subjected to a deionized water rinse to fully remove the developer or any remaining undesired portions of the coating and to stop further development. This rinsing operation (which is part of the development process) may be followed by blow drying with filtered air to remove excess water. A post-development heat treatment or bake may then be employed to increase the coating's adhesion and chemical resistance to etching solutions and other substances. The post-development heat treatment can comprise the baking of the coating and substrate below the coating's thermal deformation temperature.

In industrial applications, particularly in the manufacture of microcircuitry units on silicon/silicon dioxide-type substrates, the developed substrates may then be treated with a buffered hydrofluoric acid etching solution or plasma gas etch. The resist compositions of the present invention are believed to be resistant to a wide variety of acid etching solutions or plasma gases and provide effective protection for the resist-coated areas of the substrate. Later, the remaining areas of the photoresist coating may be removed from the etched substrate surface by conventional photoresist stripping operations. The present invention is further described in detail by means of the following Examples. All parts and percentages are by weight unless explicitly stated otherwise, and all temperatures are degrees Celsius.

EXAMPLE 1

Coupling Reaction of Vanillin to Dehydrodivanillin

A 2 liter, round bottom flask was charged with 261.7 milligrams (13085 units) of medium purity, soybean peroxidase, 600 mL water, 900 mL isopropanol, and 157.36 grams (1.0342 moles) vanillin. The mixture was heated to 45°–50° C. Over 18–24 hours, 120 mL of 30% hydrogen peroxide was then metered into the reaction mixture. The product precipitated out of solution during peroxide addition affording 127.63 grams (82% theory) of dehydrodivanillin (CAS Registry No. 2092-49-1) which has the following chemical formula:

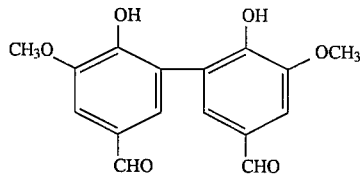

Its melting point was 307° C. (literature ca 310° C.), and it afforded the following $^1$H-NMR Spectrum:
δ= 3.95 (S, 6H)
δ= 7.45 (S, 4H)
δ= 9.85 (S, 2H)
Chemical shifts are in ppm relative to tetramethylsilane (TMS) standard. $^1$H-NMR spectrum obtained in d-DMSO.

EXAMPLE 2

Reduction of Dehydrodivanillin

Under a nitrogen atmosphere, a 500 mL flask was charged with 20 grams (0.0662 moles) dehydrodivanillin, 5.56 grams (0.147 moles) sodium borohydride, and 250 mL tetrahydrofuran (THF). The reaction mixture was then stirred for 45 minutes. 100 mL of 20% water in methanol solution were then added dropwise to the reaction mixture. The rate of addition was adjusted to maintain reflux. The mixture was stirred for 5 minutes following completion of water/methanol addition. 10 Grams of an aqueous 10% (w/v) sodium borohydride solution was added. Completion of the reaction was determined by HPLC. Once the reaction was complete, 31 mL of 20% (v/v) sulfuric acid/methanol solution was added, and the mixture was stirred for an additional 15 minutes. 20 Grams of Celite (Cas No. 61790-53-2) were then added to the mixture. The reaction mixture was then filtered and diluted to 450 mL with THF. HPLC of this solution indicates an assay of >95%. The product of this reaction was consistent with the chemical formula below:

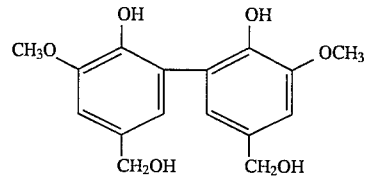

Alternatively, the product of this reaction (dehydrodivanillyl alcohol CAS No. 3626-48-0) can be isolated from this reaction mixture. The isolated product afforded the following $^1$H-NMR Spectrum:
Chemical shifts are in ppm relative to tetramethylsilane (TMS) standard. Spectrum obtained in d-DMSO.
δ= 3.85 (S, 6H)
δ= 4.45 (S, 4H)
δ= 6.7 (S, 2H)
δ= 6.9 (S, 2H)
The resulting product can be used in subsequent steps.

EXAMPLE 3

Condensation of Reduced Dehydrodivanillin With O-Cresol

Under a nitrogen atmosphere, a one liter flask was charged with 500 grams (4.624 moles) o-cresol and 2.0 mL concentrated sulfuric acid. The reaction mixture was heated, with stirring, to 85° C. 450 mL of the solution produced in Example 2 were added dropwise over 3.5 hours to the reaction mixture. Completion of reaction was determined by HPLC. The reaction mixture was cooled to <40° C. The pH of the reaction mixture was then adjusted to pH=7 by slow addition of 50% (w/w) aqueous sodium hydroxide solution. The neutralized reaction mixture was stirred at room temperature overnight.

20 Grams of Celite (CAS No. 61790-53-2) and 20 grams magnesium sulfate were added to the reaction mixture. The reaction mixture was then filtered. The filtrate was transferred to a one liter distillation flask. THF, methanol, and o-cresol were removed by vacuum distillation. The temperature of the mixture was gradually raised during the distillation until the pot temperature was 105°–115° C. and the rate of distillation was less than 1 drop/5 seconds. The contents of the flask were gradually cooled, in vacuo, to less than 70° C. The flask was adjusted to atmospheric pressure. 700 mL of water and 10 ml of acetic acid were added to the flask. The mixture was heated, with stirring, to reflux. Reflux was continued for 4 hours. The contents of the flask were cooled to room temperature. The water was decanted. 400 mL toluene were added to the flask. The contents of the flask were rapidly heated to reflux and held at reflux until a complete solution was obtained (approximately 30–45 mins.). The hot toluene solution was slowly added in a steady stream to 3.5 liters of cold hexane (ca 0° C.). The resulting solids were collected by filtration and dried at 45°–50° C. in vacuo to yield 20–25 grams of solid The solid represented a mixture which consists of 85–96% isomers corresponding to the following chemical structures and 4–15% higher molecular weight oligomers:

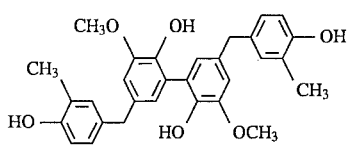

ISOMER 1

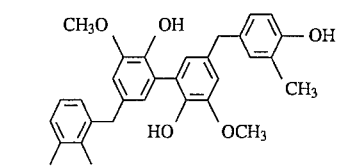

ISOMER 2

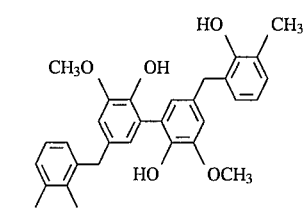

ISOMER 3

These isomers can be represented by the following general structure:

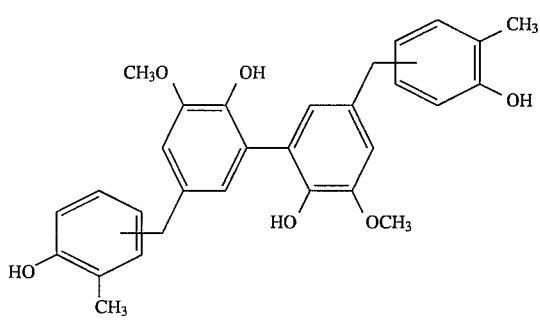

The product of this reaction afforded the following C13-NMR spectrum in d⁶-DMSO: δ= 10.37 (s); δ=15.72 (s); δ= 39.51 (m); δ= 45.59 (s); δ= 55.8 (s); δ= 111.3 (s); δ= 114.4 (s); δ= 126.3 (m); δ= 142.63 (s); δ= 147.9 (s); δ= 153.2 (s).

EXAMPLE 4

Preparation of Diazonaphthoquinone (DNQ) Photoactive Compound Rich in 3D Isomers 5.0 grams (0.0103 moles) of product of Example 3, 8.28 grams (0.0308 moles) naphthoquinone-(1,2)-diazide-(2)-5-sulfonyl chloride were dissolved in 90 mL of a 50% gamma-butryolactone/acetone solution. With stirring, 3.6 grams of triethylamine was slowly added so as to maintain the pH of the reaction mixture between 7.5–8.5. Completion of the reaction was determined by the disappearance of the starting naphthoquinone-(1,2)-diazide-(2)-5-sulfonyl chloride. The reaction mixture was acidified with 3.3 grams of acetic acid. The acidified reaction mixture was then added to 2.0 liters of vigorously stirred water. The resulting precipitate was collected by filtration, washed with fresh water and dried at 40°–45° C. under partial vacuum to yield 10 grams of a mixture of products and is rich in 3D isomers (>55%). This product mixture is referred to as DVOC3 in the TABLE 1 and has the following chemical formula:

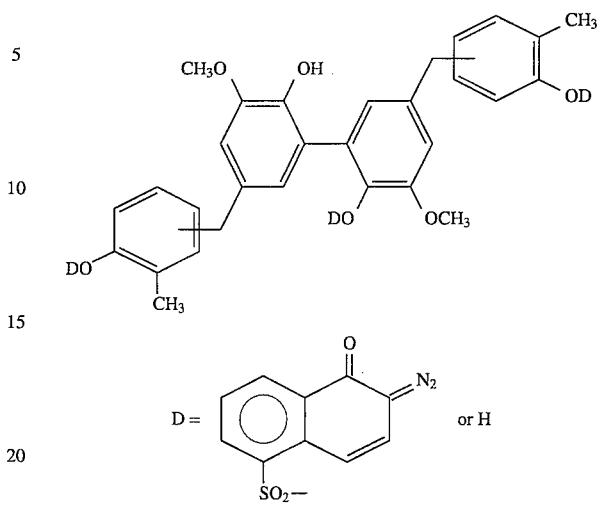

wherein, not all D groups can simultaneously be H.

The composition of DVOC3 is best described by the following HPLC:

HPLC CONDITIONS:

Column: 15 cm, 3μ Supelco C-18

Flow Rate: 1.0 mL/min.

Solvent: 60% acetonitrile/40% phosphate buffer

Detector: UV 254 nm

| HPLC Data* (% of Total Area) Retention Time (min.) of Major Components | | | |
|---|---|---|---|
| 11.6 | 12.3 | 17.5 | 20 |
| 2.71 | 5.08 | 59.79 | 13.85 |

*Retention time of components will vary as a function of solvent composition and column packing type.

EXAMPLE 5

Preparation of Diazonaphthoquinone (DNQ) Photoactive Compound Rich in 2D Isomers 7.49 grams (0.0154 moles) of product of Example 3, 8.28 grams (0.0308 moles) naphthoquinone-(1,2)-diazide-(2)-5-sulfonyl chloride were dissolved in 90 mL of a 50% gamma-butryolactone/acetone solution. With stirring, 3.6 grams of triethylamine was slowly added so as to maintain a pH of the reaction mixture between 7.5–8.5. Completion of the reaction was determined by the disappearance of the starting naphthoquinone-(1,2)-diazide-(2)-5-sulfonyl chloride. The reaction mixture was acidified with 3.3 grams of acetic acid. The acidified reaction mixture was then added to 2.0 liters of vigorously stirred water. The resulting precipitate was collected by filtration, washed with fresh water and dried at 40°–45° C. under partial vacuum to yield 10 grams of a mixture of products. This product mixture is referred to as DVOC2 in TABLE 1 and contains less than 40% of 3D isomers and greater than 48% of 2D isomers. DVOC2 has the same chemical formula as in Example 4 and is best described by the following HPLC:

HPLC CONDITIONS:

Column: 15 cm, 3μ Supelco C-18

Flow Rate: 1.0 mL/min.

Solvent: 60% acetonitrile/40% phosphate buffer

Detector: UV 254 nm

| HPLC Data (% of Total Area) Retention Time (min.) of Major Components ||||||||
|---|---|---|---|---|---|---|---|
| 4.5 | 6.1 | 8.5 | 8.9 | 11.6 | 12.3 | 17.5 | .20 |
| 4.83 | 2.085 | 14.1 | 14.2 | 5.9 | 6.6 | 37.97 | 1.04 |

EXAMPLE 6

Blend of Two Diazonaphthoquinone (DNQ) Photoactive Compound

The photoactive compounds of Examples 4 and 5 were blended together in a weight ratio of 80:20. This product is referred to as Blend 1 in TABLE 1 and is estimated to contain >67% 3D isomers, 18.4% 2D isomers and about 5.8% 1D isomers.

EXAMPLE 7

Preparation of 3-TPM—Based Photoactive Compound

The 3-TPM PAC was obtained by esterifying one mole of bis-[3,5-dimethyl-4-hydroxyphenyl]3-methoxy- 4-hydroxphenyl methane with about 2.6 moles of 2,1-diazonaphthoquinone-5-sulfonyl chloride. The chemical formula of the 3-TPM PAC is as follows:

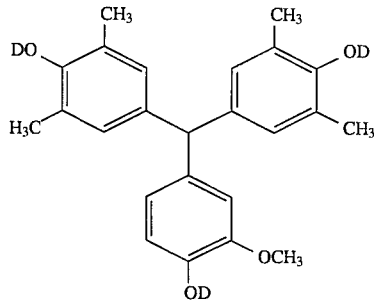

WHERE D =

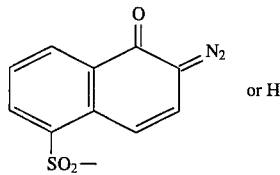

or H wherein, not all D groups can simultaneously be H.

The 3-TPM photoactive compound contained about 61–66% 3D isomers and was prepared by procedures previously described in U.S. Pat. No. 5,346,808.

EXAMPLE 8

Blend of Blend 1 and 3-TPM Photoactive Compound

The photoactive compounds of Examples 6 and 7 were blended together in a weight ratio of 70% Blend 1 and 30% 3-TPM. The resulting blend is referred to as Blend 2 on Table 1.

EXAMPLE 9

Bland of DVOC2 and 3-TPM Photoactive Compounds

The photoactive compounds of Examples 5 and 7 were blended together in a weight ratio of 70% DVOC2 and 30% 3-TPM. The resulting PAC blend is referred to as Blend 3.

EXAMPLE 10

Preparation of Photoactive Compound "A"

A three liter round bottom flask was charged with 495.5 grams (4.5 moles) resorcinol, 31.84 grams (0.5 moles) benzaldehyde, 300 mL methanol, and 15.9 grams concentrated sulfuric acid. The reaction mixture was heated to reflux and held at reflux for 2 hours. Completion of the reaction was determined by HPLC. The reaction mixture was neutralized by adding 46.5 mL triethylamine. The methanol was removed by distillation. After cooling to room temperature, 2.2 liters ethyl acetate were added to the resulting dark red oil. To this mixture, 950 mL of hexamethyldisilizane were slowly added over 9 hours. The mixture was stirred overnight. The precipitated solids were removed by filtration. The solvent and silylated resorcinol were removed from the filtrate by vacuum distillation (P<1 millitorr) at 100° C. The silylated product was distilled under reduced pressure (P<1 millitorr) at 200°–220° C.

A 150 mL flask was charged with 13.4 grams of silylated product produced above, 8 grams water, 80 mL methanol and a catalytic amount of oxalic acid. The reaction mixture was heated to reflux and held at reflux overnight. The mixture was then cooled to room temperature. Solvent was removed by vacuum distillation at 50° C. The resulting semi-solid material was dissolved in 60 mL of ethyl acetate. This solution was washed three times with fresh water. The ethyl acetate was removed by vacuum distillation at 50° C. The resulting 1 gram of solid was added to 20 grams of water. This mixture was heated to reflux and held at reflux until complete solution was obtained. The mixture was slowly cooled to room temperature during which time the product precipitated as a solid. The solid was collected by filtration and dried, in vacuo, overnight at 45°–50° C. $^1$H NMR and 13C NMR confirmed that the product was bis(2, 4-dihydroxyphenyl)phenylmethane.

The esterification of bis(2,4-dihydroxyphenyl)phenylmethane was done according to the procedure described by G. Fritz et al. (U.S. Pat. No. 3,188,210). 1 Gram (0.0032 moles) of bis(2,4-dihydroxyphenyl)phenylmethane was dissolved in a mixture of 2 mL dioxane and 2 mL dimethylformamide and the solution was combined with a solution of 1.74 grams (0.0065 moles) naphthoquinone-(1,2)-diazide-(2)-5-sulfonyl chloride in 10 mL dioxane. While stirring at room temperature, sufficient 5% aqueous sodium carbonate solution was added until a pH of 7.5–8.0 was achieved. The reaction was allowed to stir for another hour. The precipitate was separated by filtration and washed with copious amounts of water and dried, in vacuo, overnight at 45°–50° C. HPLC analysis indicated that a mixture of products was afforded. This product mixture is referred to as PAC "AA" in TABLE 1. The composition of PAC AA is best described by the following HPLC:

HPLC CONDITIONS:

Column: 15 cm, 3µ Supelco C-18

Flow Rate: 1.0 mL/min.

Solvent: 60% acetonitrile/40% phosphate buffer
Detector: UV 254 nm

| Retention Time (min.) | % of Total Area |
| --- | --- |
| 4.78 | 54.6 |
| 9.46 | 23.17 |
| 12.89 | 12.86 |

The chemical formula of PAC "AA" is as follows:

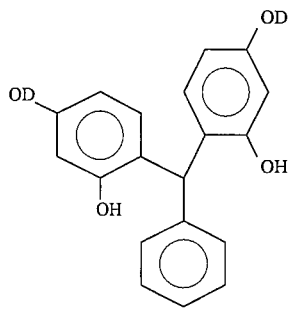

WHERE D =

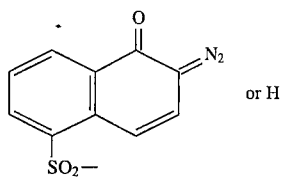

or H

PAC "AA" contained about 54% 2D isomers.

EXAMPLE 11

Blend of DVOC3 and PAC "AA" Photoactive Compounds

The photoactive compounds of Examples 4 and 10 were blended together in a weight ratio of 70% DVOC3 and 30% PAC "AA". The resulting PAC blend is referred to as Blend 4.

EXAMPLE 12

Preparation of Photoactive Compound "BB"

A one liter flask was charged with 52 grams (0.3 moles) 2,6-bis-hydroxymethyl-p-cresol (CAS No. 91- 04-3), 377.8 grams (3 moles) of 2,5-dimethylphenol (CAS No. 95-87-4), and 225 mL methanol. The reaction mixture was stirred at room temperature for 30 minutes. The reaction mixture was heated to reflux and held at reflux for 5 hours. The reaction mixture was cooled to room temperature and then added to 4 liters of stirred water. The resulting mixture was stirred overnight during which time a white solid precipitate formed. The precipitate was collected by filtration and then washed with 1 liter of fresh water. Water washing was repeated a total of four times. The precipitate was then washed with a mixture of 300 mL methylene chloride/600 mL hexane, followed immediately by a mixture of 300 mL methylene chloride/600 mL methylcyclohexane. The 10 grams of precipitate was recrystallized from a mixed solvent system containing 200 mL methylcyclohexane and 200 mL of toluene. 4 Grams of product were produced having a HPLC assay of 91%.

A one liter flask was charged with 250 mL chloroform, 8.5 mL acetone, 9.5 grams of recrystallized product from above and 13 grams (0.0484 moles) naphthoquinone-(1,2)-diazide-(2)-5-sulfonyl chloride. The reaction mixture was stirred until complete solution was obtained. Over 25 minutes, 5.4 grams (0.0534 moles) triethylamine were added dropwise while maintaining the reaction temperature of 22°±2° C. After completion of triethylamine addition, the reaction mixture was stirred at room temperature for 3 hours. 3.2 Grams of acetic acid were then added. The acidified reaction mixture was stirred for an additional 15 minutes. The solids were collected by filtration. The collected solids were redissolved in a mixture of 8 mL water and 150 mL acetone. This solution was stirred until complete solution was obtained. The acetone solution was added over 30 minutes to 2.5 liters of rapidly stirred water. The precipitate was collected by filtration and washed with copious amounts of water and dried, in vacuo, overnight at 45°–50° C. HPLC analysis indicated that a mixture of products was afforded. This product mixture is referred to as PAC "BB" in TABLE 1. The composition of PAC "BB" is best described by the following HPLC:

HPLC CONDITIONS:
Column: 15 cm, 3μ Supelco C-18
Flow Rate: 1.0 mL/min.
Solvent: 60% acetonitrile/40% phosphate buffer
Detector: UV 254 nm

| Retention Time (min.) | % of Total Area |
| --- | --- |
| 13.69 | 0.73 |
| 36.67 | 82.7 |
| 48.48 | 14.77 |

The chemical formula of the PAC "BB" is as follows:

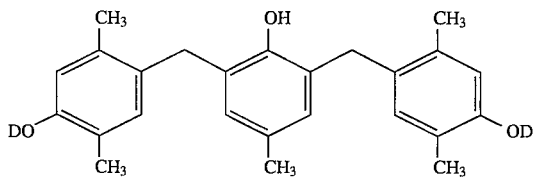

Naphthoquinone diazide esters of 2,6-bis(2',5'-dimethyl-4'-hydroxyphenylmethyl)-4-methyl-1-hydroxybenzene.

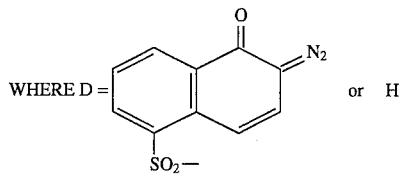

The photoactive compound "BB" contained about 82% 2D isomers.

EXAMPLE 13

Bland of DVOC3 and PAC "BB" Photoactive Compounds

The photoactive compounds of Examples 4 and 12 were blended together in a weight ratio of 70% DVOC3 and 30% PAC "BB". This resulting PAC blend is referred to as Blend 5.

EXAMPLE 14

Blend of DVOC2 and PAC "BB" Photoactive Compounds

The photoactive compounds of Examples 5 and 12 were blended together in a weight ratio of 70% DVOC2 and 30% PAC "BB". This resulting blend is referred to as Blend 6.

EXAMPLE 15

Condensation of Dehydrodivanillyl Alcohol with P-Cresol

Under a nitrogen atmosphere, a one liter flask was charged with 500 grams (4.624 moles) p-cresol and 2.0 mL concentrated sulfuric acid. The reaction mixture was heated, with stirring, to 85° C. 450 mL of the solution produced in Example 2 were added dropwise over 3.5 hours to the reaction mixture. Completion of reaction was determined by HPLC. The reaction mixture was cooled to <40° C. The pH of the reaction mixture was then adjusted to pH=7 by slow addition of 50% (w/w) aqueous sodium hydroxide solution. The neutralized reaction mixture was stirred at room temperature overnight.

20 Grams of Celite (CAS No. 61790-53-2) and 20 grams magnesium sulfate were added to the reaction mixture. The reaction mixture was then filtered. The filtrate was transferred to a one liter distillation flask. THF, methanol, and o-cresol were removed by vacuum distillation. The temperature of the mixture was gradually raised during the distillation until the pot temperature was 105°–115° C. and the rate of distillation was less than 1 drop/5 seconds. The contents of the flask were gradually cooled, in vacuo, to less than 70° C. The flask was adjusted to atmospheric pressure. 700 mL of water and 10 ml of acetic acid were added to the flask. The mixture was heated, with stirring, to reflux. Reflux was continued for 4 hours. The contents of the flask were cooled to room temperature. The water was decanted. 400 mL toluene were added to the flask. The contents of the flask were rapidly heated to reflux and held at reflux until a complete solution was obtained (approximately 30–45 mins.). The hot toluene solution was slowly added in a steady stream to 3.5 liters of cold hexane (ca 0° C.). The resulting solids were collected by filtration and dried at 45°–50° C. in vacuo to yield 20 grams of solid. The solid represents a mixture which consists of 68% corresponding to the following chemical formula and 26% higher molecular weight oligomers:

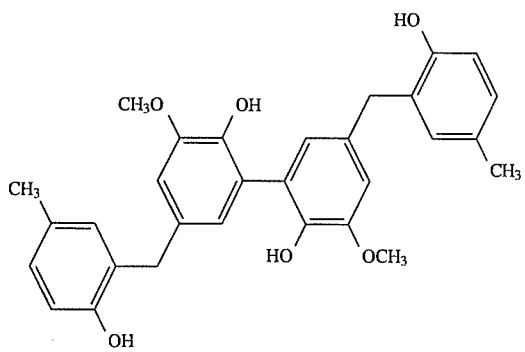

The product of this reaction afforded the following C13-NMR spectrum in $d^6$-acetone: $\delta$= 20.65 (s); $\delta$= 29.8 (m); $\delta$= 36.2 (s) $\delta$= 56.8 (s); $\delta$=113.1 (s); $\delta$= 116.2 (s); $\delta$= 129.4 (m); $\delta$= 142.8 (s); $\delta$= 148.8 (s); $\delta$= 153.5 (s).

EXAMPLE 16

Preparation of DVPC Photoactive Compound 5.0 Grams (9.0103 moles) of product of Example 15, 8.28 grams (0.0308 moles) naphthoquinone-(1,2)-diazide-(2)-5-sulfonyl chloride were dissolved in 90 mL of a 50% gamma-butyrolactone/acetone solution. With stirring, 3.6 grams of triethylamine was slowly added so as to maintain a pH of the reaction mixture between 7.5–8.5. Completion of the reaction was determined by the disappearance of the starting naphthoquinone-(1,2)-diazide-(2)-5-sulfonyl chloride. The reaction was acidified with 3.3 grams of acetic acid. The acidified reaction mixture was then added to 2.0 liters of vigorously stirred water. The resulting precipitate was collected by filtration, washed with fresh water, and dried at 40°–45° C. under partial vacuum to yield 10 grams of a mixture of products. This product mixture is referred to as DVPC in TABLE 1. The composition of DVPC is best described by the following HPLC:

HPLC CONDITIONS:

Column: 15 cm, 3μ Supelco C-18

Flow Rate: 1.0 mL/min.

Solvent: 60% acetonitrile/40% phosphate buffer

Detector: UV 254 nm

| HPLC Data (% of Total Area) Retention Time (min.) | | | | | | |
|---|---|---|---|---|---|---|
| 6.4 | 10.8 | 15 | 16.6 | 18.3 | 22 | 23.2 |
| 1.8 | 3.6 | 0 | 6.4 | 75.7 | 0.09 | 6.07 |

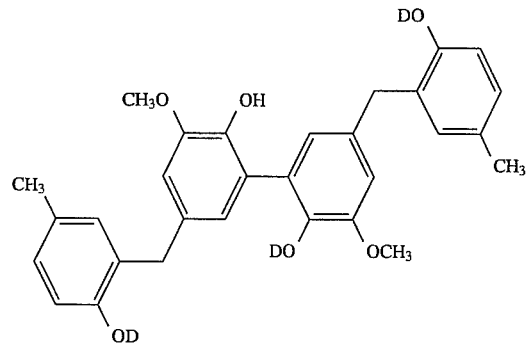

DVPC PAC

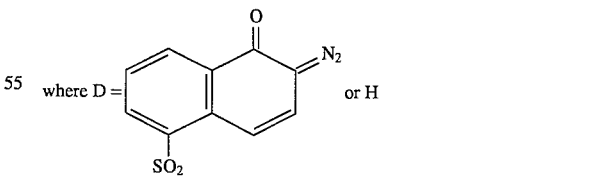

wherein not all D groups can simultaneously be H.

EXAMPLE 17

Condensation of Dehydrodivanillyl Alcohol with Phenol

Under a nitrogen atmosphere, a one liter flask was charged with 550 grams (5,844 moles) phenol and 2.0 mL concentrated sulfuric acid. The reaction mixture was heated, with stirring, to 85° C. 450 mL of the solution produced in Example 2 were added dropwise over 3.5 hours to the reaction mixture. Completion of reaction was determined by HPLC. The reaction mixture was cooled to <40° C. The pH of the reaction mixture was then adjusted to pH=7 by slow addition of 50% (w/w) aqueous sodium hydroxide solution. The neutralized reaction mixture was stirred at room temperature overnight.

20 Grams of Celite (CAS No. 61790-53-2) and 20 grams magnesium sulfate were added to the reaction mixture. The reaction mixture was then filtered. The filtrate was transferred to a one liter distillation flask. THF, methanol, and o-cresol were removed by vacuum distillation. The temperature of the mixture was gradually raised during the distillation until the pot temperature was 105°–115° C. and the rate of distillation was less than 1 drop/5 seconds. The contents of the flask were gradually cooled, in vacuo, to less than 70° C. The flask was adjusted to atmospheric pressure. 700 mL of water and 10 ml of acetic acid were added to the flask. This mixture was heated, with stirring, to reflux. Reflux was continued for 4 hours. The contents of the flask were cooled to room temperature. The water was decanted. 400 mL toluene were added to the flask. The contents of the flask were rapidly heated to reflux and held at reflux until a complete solution was obtained (approximately 30–45 mins.). The hot toluene solution was slowly added in a steady stream to 3.5 liters of cold hexane (ca 0° C.). The resulting solids were collected by filtration and dried at 45°–50° C. in vacuo to yield 20–25 grams of solid. The solid represents a mixture which consists of 61–91% isomers corresponding to the following chemical formula and 7–16% higher molecular weight oligomers:

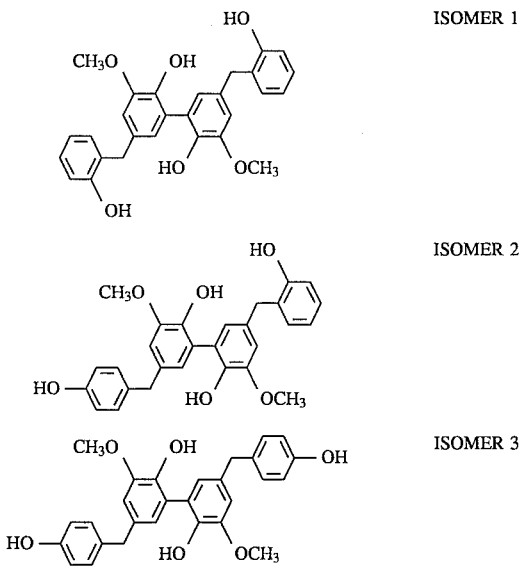

The product of this reaction afforded the following C13-NMR spectrum in d⁶-acetone: δ= 29.8 (m); δ= 35.8 (s) δ= 41.1 (s); δ= 56.5 (s); δ=112.4 (d); δ= 115.8 (s); δ= 120.3 (s); δ= 130.2 (m); δ= 142.4 (s); δ= 148.4 (d); δ= 155.9 (s).

EXAMPLE 18

Preparation of DVPH Photoactive Compound Rich in 3D Isomers 4.72 Grams (0.0103 moles) of product of Example 17, 8.28 grams (0.0308 moles) naphthoquinone-(1,2)-diazide-(2)-5-sulfonyl chloride were dissolved in 90 mL of a 50% gamma-butyrolactone/acetone solution. With stirring, 3.6 grams of triethylamine was slowly added so as to maintain a pH of the reaction mixture between 7.5–8.5. Completion of the reaction was determined by the disappearance of the starting naphthoquinone-(1,2)-diazide-(2)-5-sulfonyl chloride. The reaction was acidified with 3.3 grams of acetic acid. The acidified reaction mixture was then added to 2.0 liters of vigorously stirred water. The resulting precipitate was collected by filtration, washed with fresh water, and dried at 40°–45° C. under partial vacuum to yield 10 grams of a mixture of products. This product mixture is referred to as DVPC in TABLE 1. The composition of DVPC is best described by the following HPLC:

HPLC CONDITIONS:
Column: 15 cm, 3µ Supelco C-18
Flow Rate: 1.0 mL/min.
Solvent: 60% acetonitrile/40% phosphate buffer
Detector: UV 254 nm

| HPLC Data (% of Total Area) Retention Time (min.) | | | | | | | |
|---|---|---|---|---|---|---|---|
| 3.81 | 4.24 | 7.22 | 7.88 | 11.23 | 11.92 | 13.36 | 20.72 |
| 1.96 | 1.27 | 3.25 | 2.32 | 28.79 | 50.74 | 1.97 | 1.04 |

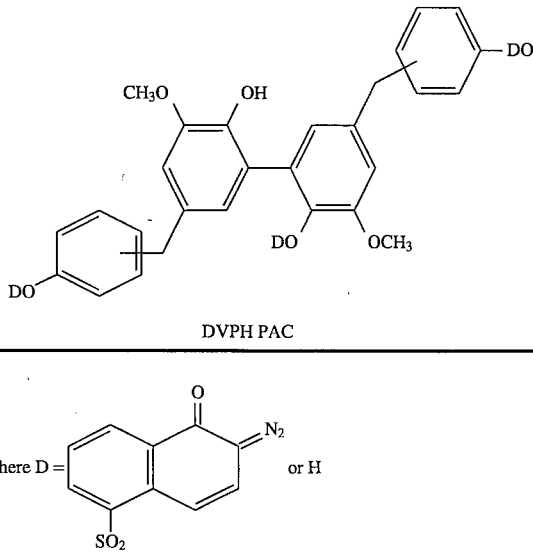

DVPH PAC wherein not all D groups can simultaneously be H.

EXAMPLE 19

Preparation of DVPH Photoactive Compound Rich in 2D Isomers 4.72 Grams (0.0103 moles) of product of Example 17, 5.53 grams (0.0206 moles) naphthoquinone-(1,2)-diazide-(2)-5-sulfonyl chloride were dissolved in 90 mL of a 50% gamma-butyrolactone/acetone solution. With stirring, 3.6 grams of triethylamine was slowly added so as to maintain a pH of the reaction mixture between 7.5–8.5. Completion of the reaction was determined by the disappearance of the starting naphthoquinone-(1,2)-diazide-(2)-5-sulfonyl chloride. The reaction was acidified with 3.3 grams of acetic acid. The acidified reaction mixture was then added to 2.0 liters of vigorously stirred water. The resulting precipitate was collected by filtration, washed with fresh water, and dried at 40°–45° C. under partial vacuum to yield 10 grams of a mixture of products. This product mixture is best described by the following HPLC:

HPLC CONDITIONS:

Column: 15 cm, 3μ Supelco C-18

Flow Rate: 1.0 mL/min.

Solvent: 60% acetonitrile/40% phosphate buffer

Detector: UV 254 nm

| HPLC Data (% of Total Area) Retention Time (min.) | | | | | |
|---|---|---|---|---|---|
| 7.22 | 7.88 | 11.23 | 11.92 | 13.36 | 20.72 |
| 14.78 | 2.35 | 10.15 | 26.64 | 0.05 | 1.16 |

EXAMPLE 20

Blend of DVPH3 with DVOC2 Photoactive Compound

The photoactive compounds of Examples 5 and 18 were blended together in a weight ratio of 24.2% DVOC2 and 75.8% DVPH3. This resulting blend is referred to as Blend 7.

EXAMPLE 21

Blend of DVPH3 with DVPH2 Photoactive Compounds

The photoactive compounds of Examples 18 and 19 were blended together in a weight ratio of 25% DVPH3 and 75% DHPH2. This resulting blend is referred to as Blend 8.

EXAMPLE 22

Blend of DVPH3 and 3-TPM Photoactive Compounds

The photoactive compounds of Examples 7 and 19 were blended together in a weight ratio of 30% 3-TPM and 70% DVPH2. This blend is referred to as Blend 9.

EXAMPLE 23

Blend of DVPH3, DVPH2, and 3-TPM Photoactive Compounds

The photoactive compounds of Examples 7, 18, and 19 were blended together in a weight ratio of 20% 3-TPM, 56% DVPH3, and 24% DVPH2. This blend is referred to as Blend 10.

PREPARATION OF NOVOLAK NO. 1

Novolak No. 1 was prepared by the procedures previously described in U.S. Pat. No. 5,346,808. The following monomer mixtures were used:

| 2,2'-dihydroxy-5,5'-dimethyl-diphenylmethane | 4.59% (w/w) |
|---|---|
| o-cresol | 1.73% (w/w) |
| 2,3-dimethylphenol | 63.9% (w/w) |
| 2,3,5-trimethylphenol | 21.92% (w/w) |
| 2,6-dimethylphenol | 7.88% (w/w) |

A formaldehyde/monomer molar ratio of 1.16 was used in the preparation of Novolak No. 1. The weight average molecular weight (Mw) of Novolak No. 1, as determined by Gel Permeation Chromatography, was 2,865. GPC results are relative to polystyrene standards.

PREPARATION OF NOVOLAK NO. 2

Novolak No. 2 was prepared by the procedures previously described in U.S. Pat. No. 5,346,808. The following monomer mixtures were used:

| 2,2'-dihydroxy-5,5'-dimethyl-diphenylmethane | 18.55% (w/w) |
|---|---|
| o-cresol | 1.75% (w/w) |
| 2,3-dimethylphenol | 49.62% (w/w) |
| 2,3,5-trimethylphenol | 22.13% (w/w) |
| 2,6-dimethylphenol | 7.94% (w/w) |

A formaldehyde/monomer molar ratio of 1.08 was used in the preparation of Novolak No. 2. The molecular weight of Novolak No. 2, as determined by Gel Permeation Chromatography, was as follows:

Mw= 2,791

Mn= 1,304

Dispersity (Mw/Mn)= 2.14

GPC results are relative to polystyrene standards.

PREPARATION OF NOVOLAK NO. 3

Novolak No. 3 was prepared according to the following procedure:

A mixture of 67.6 grams (0.625 moles) m-cresol, 38.2 grams (0.313 moles) 2.5-xylenol, 33.8 grams (0.313 moles) p-cresol, 102.3 grams (1.25 moles) 36.7% formalin solution, and 130 grams 3-ethoxyethyl propionate were placed in a 4-neck glass flask equipped with mechanical agitation, condenser, electric heating mantle, thermometer, and temperature control (thermowatch) unit. 10.5 Grams of a 10.5% (w/w) aqueous oxalic acid solution was then added. The reaction mixture was heated to 90° C. and held at 90° C. for 24 hours. The reaction mixture was cooled to room temperature. The reaction mixture was extracted three times with 150 gram portions of deionized water. Residual water which remained in the organic layer was removed by vacuum distillation. The resulting novolak solution was cooled to room temperature, then diluted with 3-ethoxyethyl propionate until the concentration of novolak in solution was 20–21% (w/w). This novolak is referred to as the "parent novolak".

A mixture of 224 grams "parent novolak", and 50 grams ethyl lactate were placed in a 4-neck glass flask equipped with mechanical agitation, condenser, electric heating mantle, thermometer, and temperature control (thermowatch) unit. The reaction mixture was heated to 60°–65° C. 880 Grams xylene were then added over one hour. The reaction mixture was maintained at 60°–65° C. for 30 minutes following completion of xylene addition. Stirring was stopped and the mixture allowed to cool to room temperature overnight. The solvent was decanted from the precipitated solid. The remaining solid novolak was dissolved in ethyl lactate. Excess ethyl lactate was removed by vacuum distillation until the concentration of novolak in solution was 37% (w/w).

The molecular weight of Novolak No. 3, as determined by Gel Permeation Chromatography, was as follows:

Mw= 13.502
Mn= 4,018
Dispersity (Mw/Mn)= 3.36
GPC results are relative to polystyrene standards.

SPEED ENHANCER SYSTEM A

TRISP-PA and trimer-p-cresol were blended together in an 80%:20% weight ratio to make Speed Enhancer A.

TRISP-PA (CAS No. 110728-28-8) is available from Mitsui Petrochemicals (America), Ltd. and has the following chemical formula and name:

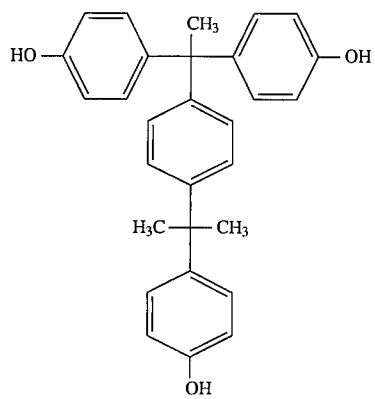

1-[1'-methyl-1'-(4'-hydroxyphenyl)ethyl]4-[1', 1'-bis-(4-hydroxyphenyl)ethyl]benzene.

Trimer-p-cresol is available from Kodak and has the following chemical formula and name:

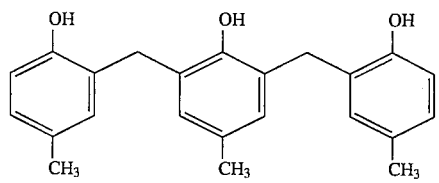

2,6-bis(2'-hydroxy-5'-methylphenylmethyl)- 4-methyl-1-hydroxybenzene.

SPEED ENHANCER SYSTEM B

DPCH (CAS No. 843-55-0) is available from Mitsui Petrochemicals (America), Ltd. under the product name Bisphenol Z and was used as Speed Enhancer B. DPCH has the following chemical formula and name:

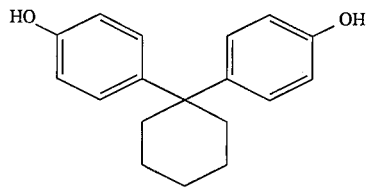

4,4'-cyclohexylidenebisphenol

EXAMPLES 24–46

Preparation of Photoresists

Twenty-three (23) photoresist formulations were prepared from products of Examples 1–23. The components were blended together in a brown glass bottle equipped with a magnetic stir bar. The resist components were added to the bottle in the following order:

1. the solvents
2. the novolak
3. the speed enhancing agents
4. the PAC's
5. leveling agent All solids were weighed out on an electronic balance having an accuracy to ±0.01 grams. The solid components were slowly added to the solvents which were stirred throughout the addition. A leveling agent (FLUORAD FC-430) was added at a concentration equal to 0.03% by weight of resist sample. When all components had dissolved, the resist samples were microfiltered directly into clean bottles. The filter which was used was a 47 mm diameter disk filter with a rated pore size of 0.2 microns.

These twenty-three formulations are set forth in TABLE 1.

TABLE 1

PHOTORESIST FORMULATIONS

| Example | PAC | % PAC | Nov. | % Nov. | Speed Enhancer | % Speed Enhancer |
|---|---|---|---|---|---|---|
| 24 | DVOC3 | 32 | 1 | 54.4 | A | 13.6 |
| 25 | DVOC3 | 32.5 | 1 | 52.1 | A | 15.4 |
| 26 | DVOC3 | 29.45 | 1 | 54.44 | A | 16.11 |
| 27 | DVOC2 | 32 | 1 | 54. 4 | A | 13.6 |
| 28 | BLEND 1 | 32.5 | 1 | 52.1 | A | 15.4 |
| 29 | BLEND 2 | 32 | 1 | 49.69 | A | 18.36 |
| 30 | DVOC3 | 32 | 2 | 49.69 | A | 18.36 |
| 31 | DVOC2 | 32 | 2 | 49.69 | A | 18.36 |
| 32 | BLEND 3 | 32 | 2 | 49.69 | A | 18.36 |
| 33 | DVOC3 | 32 | 3 | 49.69 | A | 18.36 |
| 34 | DVOC2 | 32 | 3 | 49.69 | A | 18.36 |
| 35 | DVOC2 | 40 | 1 | 43.8 | B | 16.2 |
| 36 | BLEND 4 | 32 | 1 | 49.69 | A | 18.36 |
| 37 | BLEND 5 | 32 | 1 | 49.69 | A | 18.36 |
| 38 | BLEND 6 | 32 | 1 | 49.69 | A | 18.36 |
| 39 | DVPH 3 | 27.9 | 1 | 55.64 | A | 16.46 |
| 40 | DVPH 3 | 32 | 1 | 54.4 | A | 13.6 |
| 41 | BLEND 7 | 32.5 | 1 | 52.1 | A | 15.4 |
| 42 | BLEND 8 | 32.5 | 1 | 51.97 | A | 15.52 |
| 43 | BLEND 9 | 32.5 | 1 | 54 | A | 13.5 |
| 44 | BLEND 10 | 32.5 | 1 | 49.3 | A | 18.22 |
| 45 | DVPH3 | 32.5 | 1 | 50.62 | A | 16.88 |
| 46 | DVPC | 32 | 1 | 54.4 | A | 13.6 |

COATING, SOFTBAKING, EXPOSURE, POST EXPOSURE BAKING, AND DEVELOPING OF THE PHOTORESIST

Films of the formulated photoresists were prepared for imaging, exposed, and developed according to the following general procedure:

The wafers were spin coated by applying 3 ml of photoresist formulations shown in TABLE 1 to the static wafer. The wafer was then spun at 500 rpm to spread the resist, and finally at 3,000 to 6,000 rpm to give 1.03 micron and 0.97 micron films, respectively. These photoresist coated wafers were then softbaked on a vacuum chuck hot plate at 90° C. for 60 seconds to remove residual solvent. The softbaked photoresist coated wafers were exposed for lithographic evaluation properties as well as the dissolution rate properties.

The dissolution properties and the lithographic properties were measured by exposing the softbaked wafers to 365 nm light (I-line) using a Canon stepper with a numerical aperture of 0.52. The exposure energy was controlled by the time a shutter was open allowing the light to strike the photoresist film.

After completion of exposure, the wafers were subjected to a post exposure bake (PEB) to lessen or remove the standing waves from the exposure. This was done using the vacuum chuck hot plate at 120° C. for 60 seconds. Following the PEB, the wafers were puddle-developed using 0.262N tetramethylammonium hydroxide, aqueous developer. A Perkin Elmer Development rate monitor was used to measure the dissolution rate of the exposed and unexposed areas using the same developer in a static immersion mode. The wafers exposed for lithographic evaluation were developed using a track system. The wafer remained stationary for 60 seconds while development occurs. A deionized water rinse was applied for 20 seconds while spinning, followed by dry nitrogen gas to dry the wafer. The wafer was then ready for lithographic evaluation.

Each imaged photoresist-coated substrate was evaluated for several important properties, namely the exposure threshold (Eth); Optimum photospeed (Eopt); profile of the imaged resist lines; equal line/space pair resolution (Res.); depth-of-focus of 0.40 micron line/space pairs (DOF); and resist contrast (gamma).

From the Perkin Elmer Development Rate Monitor, a plot of log dissolution rate vs. log exposure energy was generated. At low exposure, the resist has a very low dissolution rate in alkaline developer. When the exposure energies are increased, the rate of dissolution increases dramatically. The slope of this switching action was measured by taking the tangent of the angle of the slope created (tan theta). Generally, the higher the tan theta, the better the lithographic performance of the resist. This technique is used as a screening procedure to test the capability of new resins.

Both Eth and gamma were measured on exposed wafers using small exposure increments on large unpatterned areas printed across the wafer. The clearing dose for the resist film was determined visually. Gamma was determined by measuring the slope of the line relating logarithm of exposure dose with normalized resist film thickness between 70% and 20% film thickness retention.

The resist photospeed, resolution, image profiles and depth of focus (DOF) were evaluated by means of a scanning electron microscope.

The optimum exposure energy (Eopt) was determined as the energy required to replicate the dimensions of the mask for 0.5 micron line/space pairs.

The profile of the resist lines is evaluated as the ability of the photoresist to maintain a consistent width throughout the depth of the film. Very steep sidewalls are desired.

The resolving power (Res.) of the photoresist film is determined as the minimum line/space pair features which are cleared at the Eopt. The resolved features were reported in microns. Generally, the lower the resolution values, the better the resist perform.

The depth-of-focus (DOF) is a measure of the focus latitude of the photoresist corresponding to a change in the best focus used to create an image. When the focal plane of projected images is shifted above and below the resist plane, the line/space pairs created in the photoresist become deformed, due to the poor aerial image. The total range (microns), in which the focus can vary and still meet the following criteria is defined as the DOF.

The profile of the line/space pairs created at best focus should be maintained consistently throughout different focus levels. The best focus level is that which yields the maximum resolution. The width of the line of the line/space pair created at best focus (i.e., CD or critical dimension) should not vary more than 10% of nominal as the focus level is changed. The DOF for 0.40 micron line/space pairs are reported. The greater the DOF, the more desirable the photoresist becomes.

Photoresist Evaluations

The lithographic properties of these photoresists were evaluated. The results of this evaluation at various soft bake film thicknesses are provided in TABLE 2.

TABLE 2

PHOTORESIST EVALUATIONS

| Resist Example | SBFT μ | Eo mJ/cm² | Eopt mJ/cm² | Gamma | EM (Eopt/Eo) | Tan Theta | 0.4 micron DOF CD | 0.4 micron DOF Profile | Res. μ |
|---|---|---|---|---|---|---|---|---|---|
| 24 | 0.965 | 109 | 268 | 3.55 | 2.46 | 8.49 | 2.4 | 1.2 | 0.33 |
| 24 | 0.987 | 108 | 272 |  | 2.52 |  | 2.7 | 1.6 | 0.32 |
| 24 | 0.99 | 105 |  | 3.19 |  |  |  |  |  |
| 30 | 0.973 | 155 | >405 | 3.1 | <2.6 | 7.51 | 2.1 | 1.1 | 0.36 |
| 30 | 0.99 | 143 |  | 2.74 |  |  |  |  |  |
| 33 | 0.976 | 132 | >360 | 3.49 | <2.7 | 5.39 |  |  | scum |
| 33 | 0.99 | 110 |  | 3.16 |  |  |  |  |  |
| 27 | 0.972 | 47 |  | 3.04 |  | 1.6 |  |  |  |
| 27 | 0.99 | 39 |  | 3.35 |  |  |  |  |  |
| 25 | 0.973 | 110 | 256 | (7.2) | 2.33 | >9.8 | 2.4 | 1.3 | 0.34 |
| 25 | 0.99 | 101 |  | 3.65 |  |  |  |  |  |
| 25 | 1.03 | 92–101 |  | 2.94 |  |  |  |  |  |
| 26 | 0.971 | 98 | 208 | 5.8 | 2.1 | 9.06 | 2.2 | 1.2 | 0.35 |
| 26 | 0.99 | 72 |  | 4.7 |  |  |  |  |  |
|  |  |  |  |  |  |  | CD | Profile |  |
| 26 | 1.03 | 89 |  | 3.1 |  |  |  |  |  |
| 28 | 0.973 | 98 | 216 | 5.2 | 2.2 | 9.2 | 1.5 | 1.2 | 0.33 |
| 28 | 0.99 | 88 |  | 6–9 |  |  |  |  |  |
| 28 | 1.03 | 74 |  | 3.6 |  |  |  |  |  |
| 29 | 0.971 | 101 | 232 | 5.7 | 2.3 | 7.4 | 1.8 | 1.1 | 0.34 |
| 29 | 0.99 | 87 |  | 3.58 |  |  |  |  |  |
| 29 | 1.03 | 80 |  | 3.31 |  |  |  |  |  |

TABLE 2-continued

PHOTORESIST EVALUATIONS

| Resist Example | SBFT μ | Eo mJ/cm² | Eopt mJ/cm² | Gamma | EM (Eopt/Eo) | Tan Theta | 0.4 micron DOF CD | 0.4 micron DOF Profile | Res. μ |
|---|---|---|---|---|---|---|---|---|---|
| 31 | 0.967 | 65 | 98 | 3.31 | 1.5 | 4.89 | | | 0.44 |
| 31 | 0.99 | 56 | | 3.38 | | | | | |
| 32 | 0.972 | 105 | 240 | 4.31 | 2.29 | 7.05 | 2.7 | 1.2 | 0.32 |
| 32 | 0.99 | 93 | | 4.26 | | | | | |
| 32 | 1.03 | 80-88 | | 3.03 | | | | | |
| 34 | 0.97 | 50 | | 2.56 | | 0.4 | | | Poor |
| 34 | 0.99 | 41 | | 3.1 | | | | | |
| 35 | 0.97 | 47 | 98 | 4.1 | 2.08 | 6.44 | | | 0.45 |
| | | | | | | | CD | Profile | |
| 36 | 0.97 | 131 | 307.1 | 2.37 | 2.34 | 9.21 | | | 0.35 (scum) |
| 37 | 0.97 | >165 | Too slow | | | | | | |
| 38 | 0.97 | 74 | 167 | 3.55 | 2.25 | 7.04 | | | 0.42 |
| 39 | 0.97 | 74 | 162 | 4.3 | 2.2 | 9.2 | 1.3 | 1.2 | 0.37 |
| 40 | 0.97 | 92 | 207 | 4.15 | 2.3 | 8.9 | 1.8 | 1.2 | 0.35 |
| 41 | 0.97 | 68 | 135 | 4.56 | 2.0 | 7.4 | 0.8 | 0.6 | 0.37 |
| 42 | 0.97 | 68 | 153 | 4.55 | 2.3 | 8.1 | 0.8 | 0.6 | 0.36 |
| 43 | 0.97 | 62 | 101 | 3.15 | 1.6 | 3.1 | | | 0.42 |
| 44 | 0.97 | 83 | 190 | 3.33 | 2.3 | 7.5 | 1.8 | 1.4 | 0.37 |
| 45 | 0.97 | 99 | 231 | 3.25 | 2.4 | 9.0 | 1.8 | 1.1 | 0.35 |
| 46 | 0.97 | 95 | 199 | 3.63 | 2.1 | 8.65 | 1.3 | 1.2 | 0.35 |

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. The process of of forming a positive patterened image on a substrate comprising:

(1) coating said substrate with a radiation sensitive mixture useful as a positive working photoresist, said mixture comprising an admixture of an alkali soluble binder resin and a photoactive compound comprising at least one o-quinonediazide sulfonic acid ester of a phenol compound, said ester having formulae (IB) or (IIB):

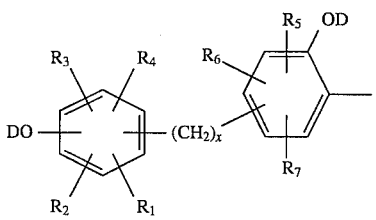
(IB)

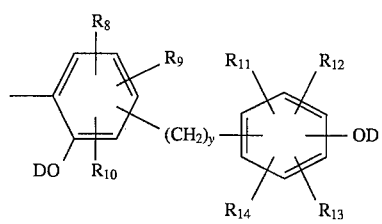

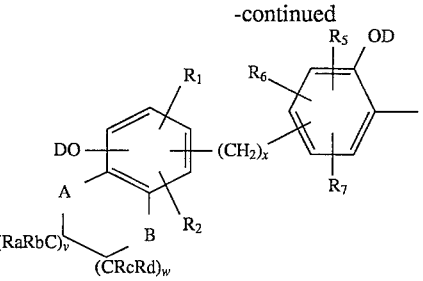
(IIB)

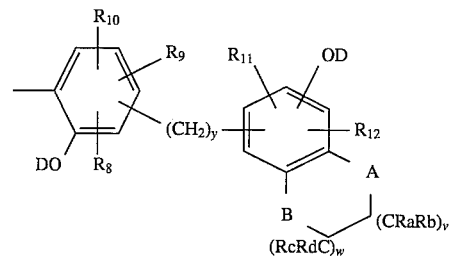

wherein $R_1$, $R_2$, $R_{11}$, and $R_{12}$ are each independently selected from the group consisting of hydrogen, OD, halogen, lower alkyl group having 1 to 4 carbon atoms; lower alkyl ether groups having 1 to 4 carbon atoms and lower alkyl thioether groups having 1 to 4 carbon atoms;

wherein $R_3$, $R_4$, $R_5$, $R_6$, $R_7$, $R_8$, $R_9$, $R_{10}$, $R_{13}$, and $R_{14}$ are each independently selected from the group consisting of hydrogen, halogen, lower alkyl groups having 1 to 4 carbon atoms, lower alkyl ether groups having 1 to 4 carbon atoms, and lower alkyl thioether groups having 1 to 4 carbon groups;

wherein x and y are each independently selected from an integer from the group 0, 1, 2, 3, and 4;

wherein Ra, Rb, Rc, and Rd are each independently selected from hydrogen and a lower alkyl group having 1 to 4 carbon atoms;

wherein v and w are each independently selected from an integer from the group 0 and 1 and each sum of v and w on a fused ring is 1 or 2; and wherein A and B are each independently selected from the group consisting of oxygen, sulfur, and a methylene radical; wherein each —OD group is a hydroxyl or an o-quinonediazide sulfonic acid ester group wherein each D is selected from the group consisting of a napthoquinonediazide sulfonyl group or benzoquinonediazide sulfonyl group and provided that at least one —OD is an o-quinonediazide sulfonic acid ester group; and wherein the amount of photoactive compound is from about 5% to about 40% by weight, based on the total solid content of said radiation sensitive mixture;

(2) subjecting said coating on said substrate to an image-wise exposure of radiation; and (3) subjecting said image-wise exposed coated substrate to a developing solution wherein the exposed area of said radiation-exposed coatings are dissolved and removed from the substrate, thereby resulting in a positive image-wise pattern in the coating.

2. The process of claim 1 wherein said radiation is ultraviolet light.

3. The process of claim 1 wherein said image-wise exposed coated substrate is subjected to a post exposure bake at a temperature from about 100° C. to about 130° C. before said development step (3).

4. The process of claim 1 wherein said developing solution comprises an aqueous solution of an alkali metal hydroxide or silicates or an aqueous solution of tetramethylammonium hydroxide.

5. The process of claim 1 wherein said photoactive compound is present in the amount of about 8% to about 30% by weight, based on the total solid content of said radiation-sensitive mixture.

6. The process of claim 1 wherein D is naphthoquinone-(1,2)-diazide-(2)-5-sulfonyl; naphthoquinone-(1,2)-diazide-(2)-4-sulfonyl or hydrogen.

7. The process of claim 6 wherein said photoactive compound has the formula (III):

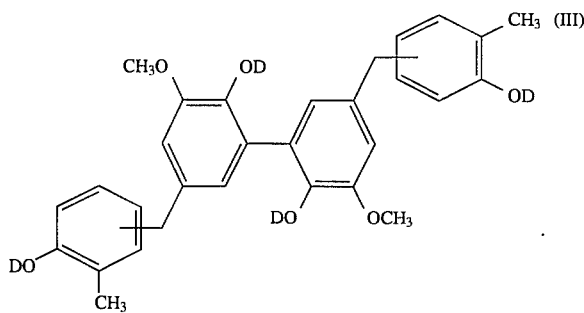

8. The process of claim 6 wherein said photoactive compound has the formula (IV):

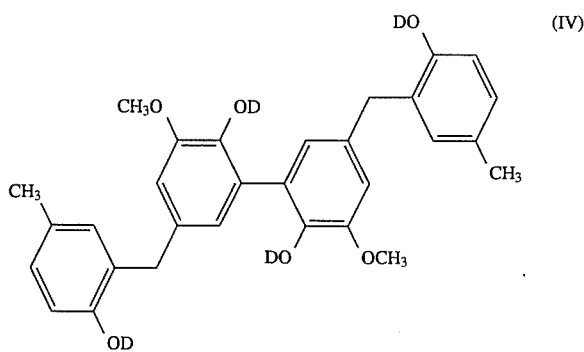

9. The process of claim 6 wherein said photoactive compound has the formula (V):

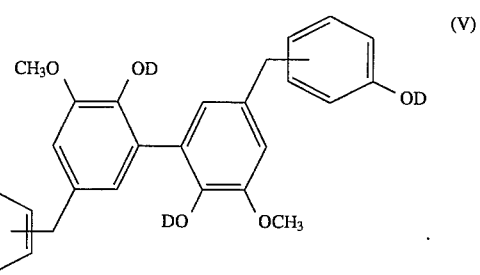

10. The process of claim 6 wherein said photoactive compound has the formula (VI):

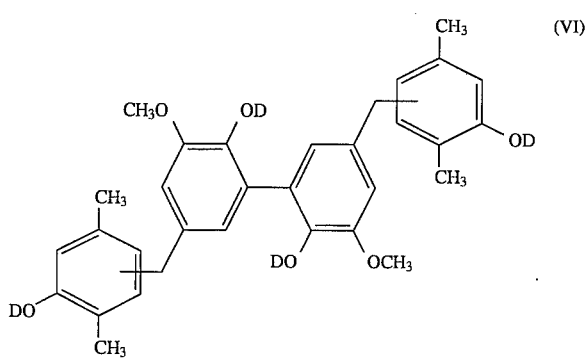

11. The process of claim 6 wherein said photoactive compound has the formula (VII):

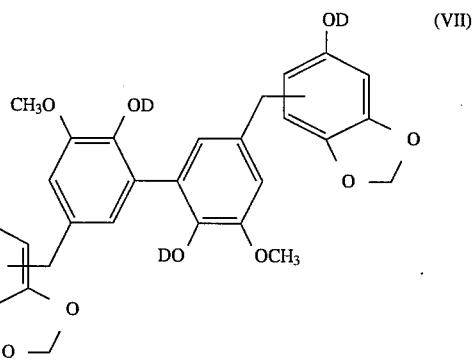

12. The process of claim 6 wherein said photoactive compound has the formula (VIII):

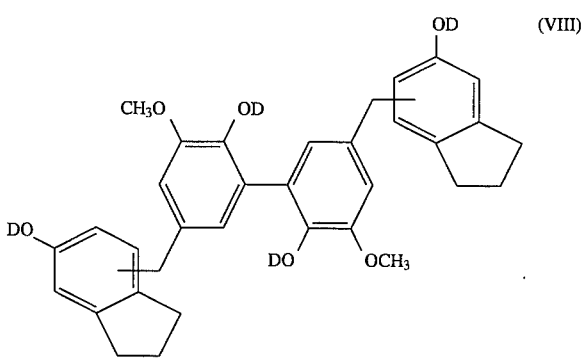

13. The process of claim 6 wherein said photoactive compound has the formula (IX):

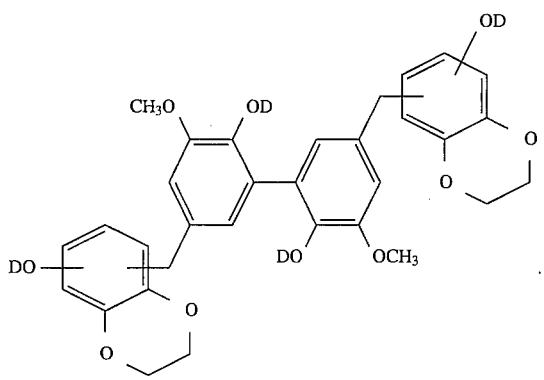
14. The process of claim 6 wherein said photoactive compound has the formula (X):
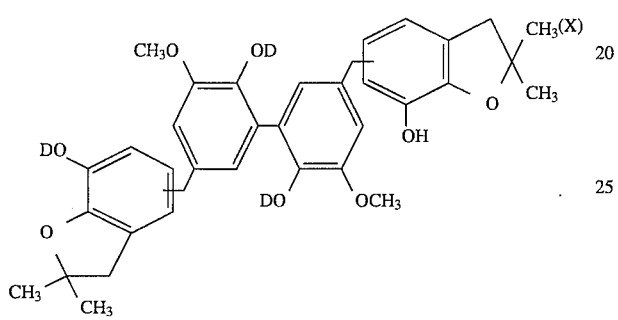
15. The process of claim 6 wherein said photoactive compound has the formula (XI):
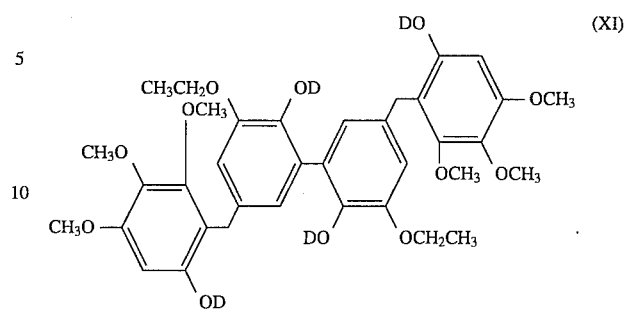
16. The process of claim 6 wherein said photoactive compound has the formula (XII):
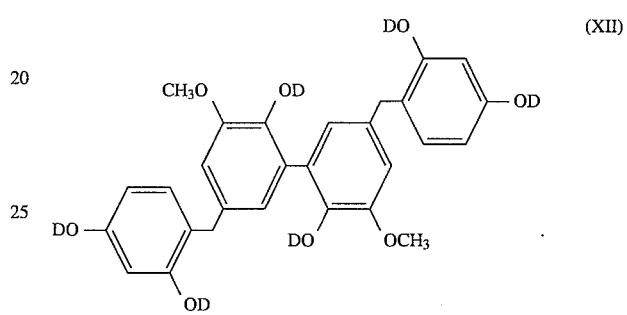
* * * * *